United States Patent [19]

Moinet et al.

[11] Patent Number: 4,504,663
[45] Date of Patent: Mar. 12, 1985

[54] 3-HYDROXYALKYL-3,4-DIHYDRO-1-SUBSTITUTED ISOQUINOLINES

[75] Inventors: Gérard H. Moinet, Orsay; Philippe L. Dostert, Paris; Guy R. Bourgery, Colombes, all of France

[73] Assignee: Delalande S.A., Courbevoie, France

[21] Appl. No.: 552,181

[22] Filed: Nov. 15, 1983

Related U.S. Application Data

[62] Division of Ser. No. 473,182, Mar. 8, 1983, Pat. No. 4,431,851, which is a division of Ser. No. 331,484, Dec. 16, 1981, Pat. No. 4,386,090.

[30] Foreign Application Priority Data

Dec. 22, 1980 [FR] France ............... 80-27252
Dec. 14, 1981 [FR] France ............... 81 23304

[51] Int. Cl.³ .................. C07D 217/16; C07D 401/04
[52] U.S. Cl. ........................ 546/144; 564/387;
564/305; 260/243.3; 564/433; 564/437;
260/245.7; 568/808; 544/106; 544/111;
544/124; 544/128; 544/173; 544/178; 544/359;
544/360; 544/363; 544/396; 544/396; 544/397;
544/399; 544/403; 546/194; 546/205; 546/255;
546/264; 546/340; 548/576; 548/578; 549/498;
549/499; 556/482; 562/462; 564/168; 564/169;
564/184; 564/337; 564/366
[58] Field of Search ........................... 546/144, 150

[56] References Cited

U.S. PATENT DOCUMENTS

2,168,929 8/1939 Bockmühl et al. ............ 546/144
3,663,608 5/1972 Holava et al. ............... 568/808
3,663,627 5/1972 Juby et al. ................. 568/808
3,704,328 11/1972 Kaltenbronn ............... 568/808
3,891,654 6/1975 Valette ..................... 546/144

OTHER PUBLICATIONS

Moinet et al., "Chemical Abstracts", vol. 97, 1982, col. 216027q.

*Primary Examiner*—Glennon H. Hollrah
*Assistant Examiner*—James H. Turnipseed
*Attorney, Agent, or Firm*—Flynn, Thiel, Boutell & Tanis

[57] ABSTRACT

The present invention concerns novel heterocyclic aminoalcoyl derivatives having the formula:

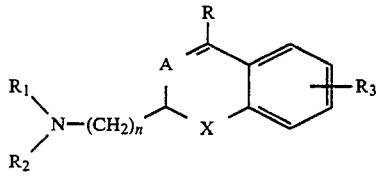

wherein n=1, 2 or 3; A represents a nitrogen atom or the CH group, X=$CH_2$ or $CH_2O$; R represents a phenyl nucleus possibly substituted; $NR_1R_2$=amino, methylamino, N,N-dialkylamino or an heterocyclic radical; and $R_3$=H, halogen, alkyl, alkyloxy or methoxy.

These derivatives are useful as drugs, especially as analgesics and antidepressants.

2 Claims, No Drawings

3-HYDROXYALKYL-3,4-DIHYDRO-1-SUBSTITUTED ISOQUINOLINES

This is a division of application Ser. No. 473,182, filed Mar. 8, 1983, now U.S. Pat. No. 4,431,851 which in turn is a division of application Ser. No. 331,484, filed Dec. 16, 1981, now U.S. Pat. No. 4,386,090.

The present invention relates to new heterocyclic aminoalcoyl derivatives and more exactly new derivatives of 3,4-dihydro naphthalene, 3,4-dihydro isoquinoline and 2,3-dihydro benzoxazepine [1-4] substituted in position 3 by an aminoalkyl chain, the process for preparing same and the therapeutical use thereof.

These new derivatives correspond more exactly to the general formula:

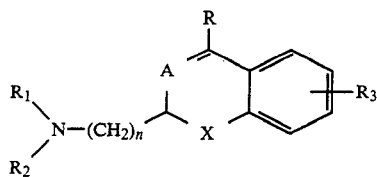
(I)

in which:

n=1, 2 or 3;

A represents the nitrogen atom or a CH group;

X represents either the methylene group ($CH_2$), or the methylene oxy group ($CH_2$—O), A not being able to represent the CH group in this latter case;

R represents a phenyl or ortho-fluorophenyl nucleus when A represents the CH group; and either a phenyl nucleus substituted or not by a halogen atom, a nitro group, an alkyl group of 1 to 4 carbon atoms, an alkyloxy group of 1 to 4 carbon atoms or a trifluoromethyl group, or a pyridinic nucleus or a cyclohexyl group, when A represents the nitrogen atom;

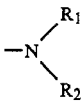

represents a group chosen from the following: amino, methylamino, N,N-dialkylamino whose alkyl groups each comprise from 1 to 4 carbon atoms, pyrrolidino, piperidino, morpholino, (4-methyl) piperazino;

not however being able to assume the amino or methylamino value when X represents the methyleneoxy group ($CH_2O$) or when (A, X, n) assumes the value ($N, CH_2$, 1); and $R_3$ represents either a hydrogen atom in the case where A represents the CH group, or a halogen atom, a hydrogen atom, an akyl group of 1 to 4 carbon atoms, an alkyloxy group of 1 to 4 carbon atoms or two methoxy groups in the case where A represents a nitrogen atom.

Among the compounds of the invention, there may be mentioned as particularly interesting those in which R represents the phenyl and ortho-fluorophenyl nuclei and

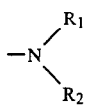

represents the group

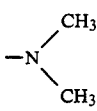

The present invention relates also to the pharmaceutically acceptable organic or mineral acid addition salts of the formula (I) compounds.

Furthermore, the present invention relates to processes for preparing the formula (I) compounds, which processes are described below.

A: The compounds (I) for which A represents the CH group are obtained:

either by condensation of the lithium derivative of bromobenzene, preferably in an ether medium, with the compounds of formula:

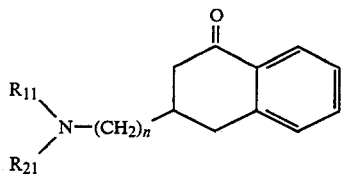
(II)

in which n=1, 2 or 3 and

represents a N,N-dialkylamino group in which the alkyl groups each comprise 1 to 4 carbon atoms or a pyrrolidino, piperidino, morpholino or (4-methyl) piperazino radical, this condensation being possibly followed by dehydration, preferably by means of a mineral acid in an alcohol medium, when the intermediate hydroxylated compounds formed are not spontaneously dehydrated during the reaction, which leads to the formula (I) compounds in which A represents the CH group and R=phenyl;

or by condensation of the amines of formula:

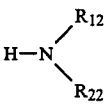
(III)

where

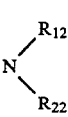

has the same meaning as

in (I) except for the amino group, respectively on the mesylates of the compounds of formula:

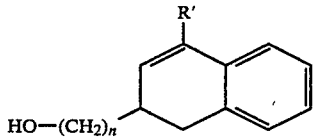
(IV)

where n=1, 2 or 3 and R' represents a phenyl or orthofluorophenyl group, or by condensation of phthalimide on these same mesylates followed by the hydrazinolysis of the intermediates obtained, said mesylates resulting from the action of mesyl chloride, preferably in the presence of triethylamine and in a methylene chloride medium, on compounds (IV), which leads to the formula (I) compounds in which A represents the CH group and R=phenyl or o-Fphenyl.

Compounds (II) are obtained by oxidation, preferably by means of manganese dioxide (MnO$_2$) and in a chloroform medium, of the compounds of formula:

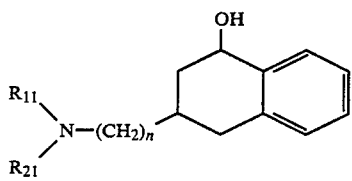
(V)

in which n and

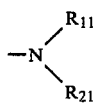

have the same meanings as in (II).

Compounds (V) are obtained by reduction, preferably by means of lithium aluminium hydride in a T.H.F. medium, of the compounds of formula:

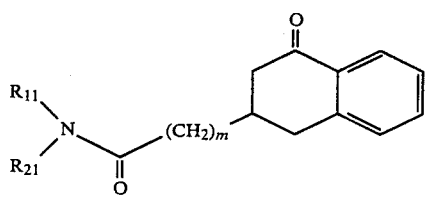
(VI)

in which m=0, 1 or 2 and

have the same meanings as in (V).

The compounds of formula (VI) are obtained by the so-called "BOISSONNAS" reaction of the amines of formula:

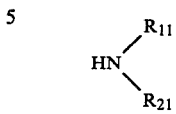
(VII)

where

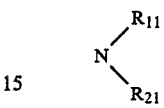

has the same meanings as in (VI), respectively on the acids of formula:

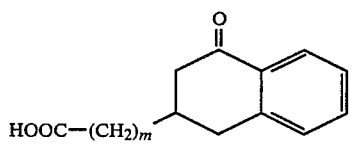
(VIII)

in which m=0, 1 or 2.

As for compounds (IV), they are obtained by condensation of the lithium derivatives of bromo-benzene or 1-bromo 2-fluoro benzene, preferably in a T.H.F. medium with the compounds of formula:

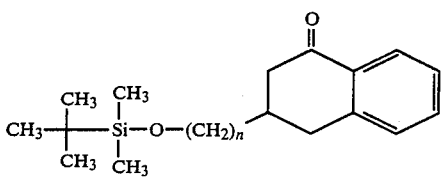
(IX)

in which n=1, 2 or 3.

Compounds (IX) are obtained by the action of tertiobutyldimethylsilyl chloride in the presence of imidazol and in a dimethylformamide medium on the compounds of formula:

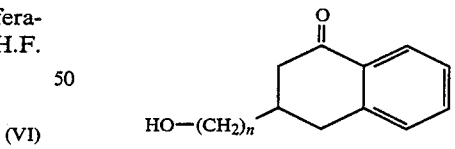
(X)

in which n=1, 2 or 3.

Compounds (X) are obtained by a four stage synthesis from the compounds of formula (VIII) which consists (1) in treating compounds (VIII) with hydrochloric ethanol in a benzene and ethanolic medium, (2) in condensing ethane dithiol on the keto-ester thus obtained, in the presence of boron trifluoride etherate in a methylene chloride medium, (3) in reducing the ester group of the compound thus obtained into a hydroxymethyl group by means of lithium aluminium hydride in a T.H.F. medium and finally (4) in removing the protection of the ketone function by treatment with methyl iodide in an aqueous methanol medium.

B. The compound of formula (I) in which A represents the nitrogen atom and X represents the methylene (CH$_2$) or methyleneoxy (CH$_2$O) group, except for those in which

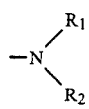

represents the amino or methylamino group, are obtained by a process which consists in cyclizing, preferably in the presence of phosphorous oxychloride and in an inert solvent such as methylene chloride for example, the compounds of formula:

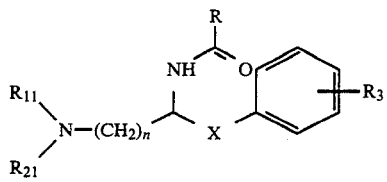 (XI).

in which NR$_{11}$R$_{21}$ represents a N,N-dialkylamino group in which each of the alkyl groups comprises 1 to 4 carbon atoms, or a pyrrolidino, piperidino, morpholino or (4-methyl) piperazino group, n, X, R and R$_3$ having the same meanings as in formula (I) when A represents therein the nitrogen atom.

The novel compounds of formula (XI), in which (n, X) assumes the value (1, CH$_2$) are obtained by reduction, preferably by means of lithium aluminium hydride in a tetrahydrofuran medium, of the compounds of formula:

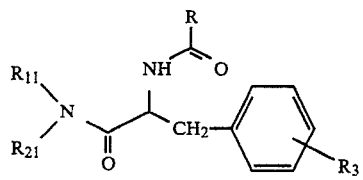 (XII)

in which R,

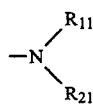

and R$_3$ have the same meanings as in formula (XI).

The novel compounds of formula (XII) are obtained by the so-called "BOISSONNAS" reaction of the amines of formula (VII), respectively with the acids of formula:

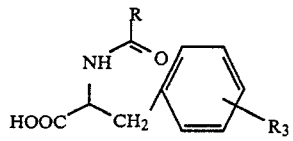 (XIII)

in which R and R$_3$ have the same meanings as in formula (XII).

The novel compounds of formula (XI), in which (n, X) assumes the value (2, CH$_2$), (3, CH$_2$), (1, CH$_2$O), (2, CH$_2$O) or (3, CH$_2$O) are obtained by the action of acid chlorides of formula:

R—COCl (XIV)

in which R has the same meanings as in formula (I) when A represents therein a nitrogen atom, respectively on the compounds of formula:

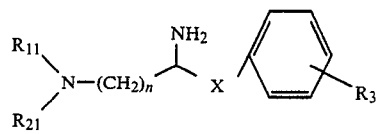 (XV)

in which n, X,

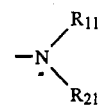

and R$_3$ have the same meanings as in formula (XI), (n, X) not however being able to assume the value (1, CH$_2$). This reaction takes place preferably in a tetrahydrofuran medium and in the presence of triethylamine.

The compounds of formula (XV) in which n takes the value 2 are obtained by reduction, preferably by means of lithium aluminium hydride, of the compounds of formula:

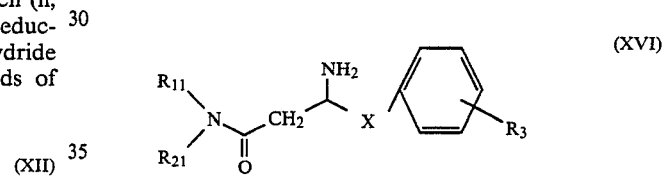 (XVI)

in which X,

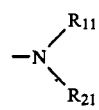

and R$_3$ have the same meanings as in formula (XV).

The compounds of formula (XVI) are obtained by reduction, preferably by means of sodium borohydride in acetic acid, of the compounds of formula:

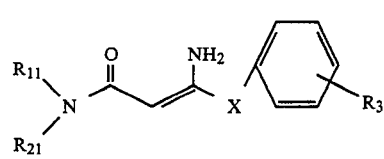 (XVII)

in which X,

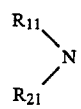

and R$_3$ have the same meanings as in formula (XVI).

The compounds of formula (XVII) are obtained by condensation, preferably in an autoclave and in an ethanol medium, of ammonia with the compounds of formula:

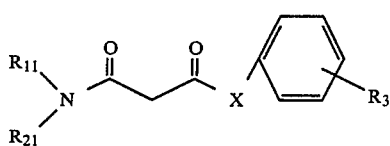 (XVIII)

in which X,

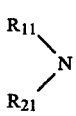

and R₃ have the same meanings as in formula (XVII).

The compounds of formula (XVIII) are obtained by acid hydrolysis, preferably in an acetone medium, of the compounds of formula:

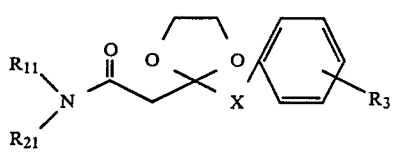 (XIX)

in which X,

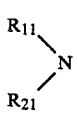

and R₃ have the same meanings as in formula (XVIII).

The compounds of formula (XV) in which n=3 are obtained by reduction preferably by means of lithium aluminium hydride of the compounds of formula:

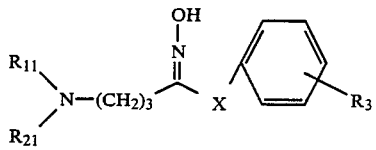 (XX)

in which X,

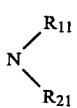

and R₃ have the same meanings as in formula (XV).

The compounds of formula (XX) are obtained by action of hydroxylamine on the compounds of formula:

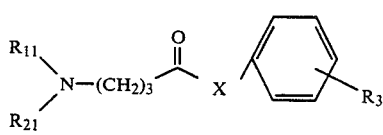 (XXI)

in which X,

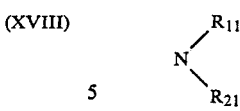

and R₃ have the same meanings as in formula (XX).

The compounds of formula (XXI) are obtained by acid hydrolysis, preferably in an acetone medium, of the compounds of formula:

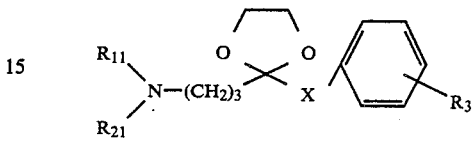 (XXII)

in which X,

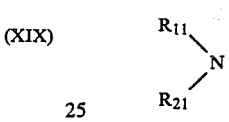

and R₃ have the same meanings as in formula (XXI).

The compounds of formula (XXII) are obtained by reduction, preferably by means of lithium aluminium hydride, of the compounds of formula:

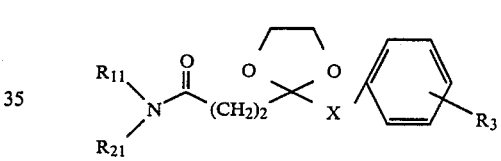 (XIXa)

in which X,

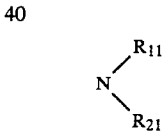

and R₃ have the same meanings as in formula (XXII).

The compounds of formulae (XIX) and (XIXa) are obtained by so-called "BOISSONNAS" reaction of the amines of formula (VII) respectively with the acids of formula:

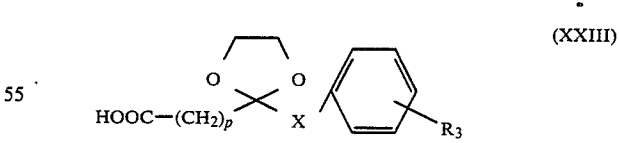 (XXIII)

in which p takes the value 1 or 2, X and R₃ having the same meanings as in formula (XIX) or (XIXa).

The compounds of formula (XXIII) are obtained by saponification of the esters of formula:

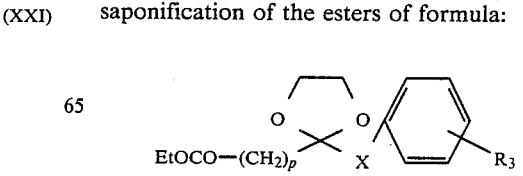 (XXIV)

in which X, p and R₃ have the same meanings as in formula (XXIII).

The esters of formula (XXIV) are obtained by reaction of ethylene glycol, in the presence of paratoluene sulfonic acid, on the keto-esters of formula:

$$EtOCO-(CH_2)_p-CO-X\underset{R_3}{\underbrace{\bigcirc}} \quad (XXV)$$

in which X, p and R₃ have the same meanings as in formula (XXIV).

The novel compounds of formula (XV), in which (n, X) takes on the value (1, CH₂—O) are obtained by hydrogenolysis, preferably in the presence of palladium on charcoal, of the compounds of formula:

$$\underset{R_{21}}{\overset{R_{11}}{N}}-CH_2-\underset{\phi}{\overset{\phi}{N}}-O-\underset{R_3}{\bigcirc} \quad (XXVI)$$

in which $$N\underset{R_{21}}{\overset{R_{11}}{\diagup}}$$

and R₃ have the same meanings as in formula (XV).

The compounds of formula (XXVI) are obtained by action, in an ethanol medium, of the amines of formula (VII) respectively on the compounds of formula:

$$\underset{\phi}{\overset{\phi}{N}}\diagdown\underset{Cl}{\diagup}O-\underset{R_3}{\bigcirc} \quad (XXVII)$$

in which R₃ has the same meanings as in formula (XXVI).

The compounds of formula (XXVII) are obtained by action of thionyl chloride, preferably in a methylene chloride medium, on the compounds of formula:

$$\underset{\phi}{\overset{\phi}{N}}\diagdown\underset{OH}{\diagup}O-\underset{R_3}{\bigcirc} \quad (XXVIII)$$

in which R₃ has the same meanings as in formula (XXVII).

C. The compounds of formula (I) in which A represents the nitrogen atom, X represents the methylene group, n takes the value 2 or 3 and $$-N\underset{R_2}{\overset{R_1}{\diagup}}$$

represents an amino group are obtained by a process which consists in a hydrazinolysis of the compounds of formula:

in which q takes the value 2 or 3, R and R₃ having the same meanings as in formula (I) when A represents therein the nitrogen atom, the compounds of formula (XXIX) being obtained by condensation of phthalimide with the compounds of formula:

$$MsO-(CH_2)_q\underset{}{}\overset{R}{\underset{N}{\diagdown}}\underset{R_3}{\bigcirc} \quad (XXX)$$

in which q, R and R₃ have the same meanings as in formula (XXIX).

D. The compounds of formula (I) in which A represents the nitrogen atom, X represents the methylene group, n assumes the value 2 or 3 and $$-N\underset{R_2}{\overset{R_1}{\diagup}}$$

represents a methylamino group, a N,N-dialkylamino group in which the alkyl groups have from 1 to 4 carbon atoms or a pyrrolidino, piperidino, morpholino or (4-methyl) piperazino group are obtained by condensing the compounds of formula (XXX) respectively with methylamine or the amines of formula (VII).

The compounds of formula (XXX) are obtained by action of mesyl chloride on the compounds of formula:

$$HO-(CH_2)_q\underset{}{}\overset{R}{\underset{N}{\diagdown}}\underset{R_3}{\bigcirc} \quad (XXXI)$$

in which q, R and R₃ have the same meanings as in formula (XXX).

The compounds of formula (XXXI) are obtained by action of sodium carbonate in a methanol medium on the compounds of formula:

$$CH_3COO-(CH_2)_q\underset{}{}\overset{R}{\underset{N}{\diagdown}}\underset{R_3}{\bigcirc} \quad (XXXII)$$

in which q, R and R₃ have the same meanings as in formula (XXXI).

The compounds of formula (XXXII) are obtained by cyclization by means of phosphorous oxychloride of the compounds of formula:

$$\text{(XXXIII)}$$

in which q, R and R₃ have the same meanings as in formula (XXXII).

The compounds of formula (XXXIII) are otained by acetylation of the compounds of formula:

$$\text{(XXXIV)}$$

in which q, R and R₃ have the same meanings as in formula (XXXIII).

Finally, the compounds of formula (XXXIV) are obtained by reduction, preferably by means of lithium aluminium hydride, of the compounds of formula:

$$\text{(XXXV)}$$

in which p takes on the value 1 or 2, R and R₃ having the same meanings as in formula (XXXIV).

E. Compounds (IV) in which n assumes the value 3 may also be obtained by reduction, by means of lithium aluminium hydride in a T.H.F. medium, of the compounds of formula:

$$\text{(XXXVI)}$$

in which R' has the same meanings as in (IV).

Compounds (XXXVI) are obtained by action of hydrochloric ethanol, in an ethanol medium, on the compounds of formula:

$$\text{(XXXVII)}$$

in which R' has the same meanings as in (XXXVI).

Compounds (XXXVII) are obtained by a two stage synthesis which consists in reacting mesyl chloride, in the presence of triethylamine, on compounds (IV) in which n assumes the value 2 in solution in methylene chloride, then in treating the intermediate compounds thus obtained by means of sodium cyanide in solution in dimethylsulfoxide.

The salts of the compounds of formula (I) will be obtained in a conventional way, for example by the action of an acid in solution in an appropriate solvent, on the compounds (I) themselves also in solution in an appropriate solvent.

The following preparations are given by way of example to illustrate the invention.

EXAMPLE 1

3-Dimethylaminomethyl 1-phenyl 3,4-dihydro naphthalene, oxalate (I)

Code number: 1

1st step: 3-Dimethylaminocarbonyl 1-tetralone (VI)

To a solution cooled to 0° C. of 9.5 g of 2-(1,2,3,4-tetrahydro 4-one naphthalene yl carboxylic acid and 7.6 ml of triethylamine in 100 ml of tetrahydrofuran are added 5.7 ml of ethyl chloroformiate. Then after 30 minutes at 0° C., 23 g of dimethylamine are slowly added, and it is left to return to ambient temperature. Then the T.H.F. is evaporated, the residue is taken up in water, extracted with chloroform, washed with a dilute NaOH solution (1 N), with water, then with a dilute hydrochloric acid solution (1 N), dried on sodium sulfate, filtered and the filtrate evaporated. Thus 7.1 g (65%) of the expected product are obtained, in the form of an oil which is crystallized from isopropylic ether. Melting point: 190° C.

2nd step: 3-Dimethylaminomethyl 1-hydroxy 1,2,3,4-tetrahydro naphthalene

A suspension of 2 g of the compound of formula (VI) obtained in the preceding step and 0.76 g of lithium hydride in 200 ml of T.H.F. is left under agitation at ambient temperature for 24 hours. Then it is hydrolyzed with wet sodium sulfate, filtered and the solvent evaporated. An oil is obtained [NMR spectrum (CDCl₃) δppm=7.25, m, 4 aromatic protons; 4.8, m, proton in α of —OH; 3.8, m, 3 OH protons and two protons in 2 and 4; 2.2, m, 11 protons:

$$-CH_2-N\begin{array}{c}CH_3\\CH_3\end{array}$$

and 3 protons in 2, 3 and 4] which is used in the crude state in the next step.

3rd step: 3-Dimethylaminomethyl 1-tetralone hydrochloride (II)

A mixture of 9.4 g of the compound of formula (V) obtained in the preceding step and 110 g of manganese dioxide (MnO₂) in 600 ml of chloroform is left under agitation for two hours at ambient temperature. Then it is filtered, the filtrate evaporated and the crude product obtained purified on an alumina column. By elution with the petroleum ether (80%)—ethyl acetate (20%) mixture, 6.4 g (yield 69%) of a product are obtained which is dissolved in isopropylic alcohol. Then hydrochloric ethanol is added and the precipitate filtered which possesses the following characteristics:

Melting point: 144° C.
Molecular weight: 239.74.
Empirical formula: $C_{13}H_{18}ClNO$.
Elementary analysis:

|  | C | H | N |
|---|---|---|---|
| Calculated (%) | 65.12 | 7.57 | 5.84 |
| Obtained (%) | 65.24 | 7.87 | 6.05 |

4th step: 3-Dimethylaminomethyl 1-phenyl 1-hydroxy 1,2,3,4-tetrahydro naphthalene To a solution of 3 g of lithium in 10 ml of ether are slowly added 23 ml of bromobenzene in 100 ml of ether. Then 11 g of the compound of formula (II) (in base form) obtained in the preceding step in 15 ml of toluene are added. The ether is evaporated and the toluene solution left at reflux for 8 hours. Then the solvent is evaporated and the residue chromotographed on an alumina column. By elution with the petroleum ether (80%)—ethyl acetate (20%) mixture, 4 g of the expected product are obtained which is in the form of an oil.

Yield: 26%

NMR spectrum (CDCl$_3$) δppm=7.3, m, 9 aromatic protons; 2.3 to 3.8, m, 6 OH protons and protons in 2,3 and 4; 2.3, m, 8 protons in α of the amine.

5th step: 3-Dimethylaminomethyl 1-phenyl 3,4-dihydro naphtalene oxalate (I)

Code number: 1

A solution of 5.5 g of the compound obtained in the preceding step in 50 ml of ethanol and 50 ml of hydrochloric alcohol ≃ 4 N is left under agitation at ambient temperature for 20 hours. Then, the solvent is evaporated, the residue taken up in water, basified with 1 N aqueous NaOH, extracted with methylene chloride, washed with water, dried on sodium sulfate, filtered, the solvent evaporated, the residue taken up in acetone and an oxalic acid acetone solution is added. Thus, 3.2 g of the expected product are obtained.

Yield: 64%.
Melting point: 100° C.
Molecular weight: 353.40.
Empirical formula: C$_{19}$H$_{23}$O$_4$N.
Elementary analysis:

|  | C | H | N |
|---|---|---|---|
| Calculated (%) | 71.37 | 6.56 | 3.96 |
| Obtained (%) | 71.44 | 6.55 | 3.82 |

By the same process, but from the corresponding reagents, the compound of formula (I) under code number 2 in table I below is obtained.

EXAMPLE 2

5-chloro 3-dimethylaminoethyl 1-phenyl 3,4-dihydro-isoquinoline hydrochloride

Code number: 18

A suspension of 32 g of 1-dimethylamino 3-benzamido 4-orthochlorophenyl butane [(XI), code number 57] in 350 ml phosphorous oxychloride were brought to 100° C. for 12 hours. Then the solvent is evaporated, the residue taken up in water, basified with concentrated aqueous NaOH, extracted with methylene chloride, filtered, the filtrate evaporated and the product obtained chromatographed on an alumina column (elution by means of methylene chloride). Then the product obtained is dissolved in ether, hydrochloric ethanol is added and the precipitate formed is filtered.

Yield: 57%.
Melting point: 200° C.
Molecular weight: 385.76.
Empirical formula: C$_{19}$H$_{23}$Cl$_3$N$_2$+1/6 H$_2$O.

|  | C | H | N |
|---|---|---|---|
| Calculated (%) | 58.78 | 6.05 | 7.21 |
| Obtained (%) | 56.68 | 6.04 | 7.30 |

By the same process but from the corresponding reagents, the compounds of formula (I) were obtained, appearing under code numbers 6 to 14, 17, 19, 22 to 45, 86 to 88, 94 to 100 and 102 to 108 in tableau I below.

EXAMPLE 3

N-benzoyl α(N,N-dimethylaminomethyl) phenethylamine [(XI, X=CH$_2$, n=1]

Code number: 47

1st step: N-benzoyl α(N,N-dimethylaminocarboxyl) phenetylamine (XII)

To a solution of 26.5 g of N-benzoyl phenylalanine (XIII) in 200 ml of T.H.F. are added 11 g of triethylamine, it is cooled to 0° C. and 11 g of ethyl chloroformiate are added. After 30 mn at 0° C., a solution of 4.5 g of diethyllamine in 50 ml of T.H.F. is added, then it is left for 2 hours at ambient temperature. Then the solvent is evaporated, the residue taken up in water, extracted with chlorofrom, dried on sodium sulfate, filtered and the filtrate evaporated. Thus, the expected product was obtained with a yield of 81% Melting point: 150° C.

2nd step: N-benzoyl α(N,N-dimethylaminomethyl) phenetylamine (XI)

Code number: 47

A suspension of 12 g of the compound of formula (XII) obtained in the preceding step in 100 ml of T.H.F. is slowly added to a suspension of 2.2 g of AlLiH$_4$ in 100 ml of T.H.F. Then it is brought to reflux for two hours, hydrolized by means of wet sodium sulfate, filtered and the filtrate evaporated. Thus the expected compound is isolated.

Yield: 68%.
Melting point: 110° C.
Molecular weight: 282.39.
Empirical formula: C$_{18}$H$_{22}$N$_2$O.
Elementary analysis:

|  | C | H | N |
|---|---|---|---|
| Calculated (%) | 76.56 | 7.85 | 9.92 |
| Obtained (%) | 76.26 | 8.02 | 10.03 |

By the same process, but from the corresponding reagents, the compounds of formula (XI) are obtained appearing under code numbers 48 to 55 and 109 to 115 in table II below.

EXAMPLE 4

1-Dimethylamino 3-benzamido 4-orthochlorophenyl butane [(XI), X=CH$_2$, n=2]

Code number: 57

1st step: N,N-dimethyl [4-(orthochlorophenyl) 3-oxo] butanamide [(XVIII), X=CH$_2$]

To a solution of 80 g of N,N-dimethyl 2-[2-(orthchlorobenzyl) 1,3-dioxolan] yl acetamide (XIX) in 1000 ml of acetone are slowly added 35 ml of concentrated hydrochloric acid. Then it is left under agitation for 12 hours, neutralized with sodium carbonate, filtered, the filtrate evaporated, diluted in water, extracted with ether, washed with water, dried on sodium sulfate, filtered and the filtrate evaporated. 53 g of the expected compound are obtained.

Yield: 79%.

| NMR spectrum | |
|---|---|
| (CDCl₃)δppm | = 7.25, m (benzenic protons) |
| | = 4.00, s, (φ-CH₂—CO—) |
| | 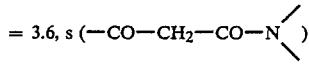 |
| | 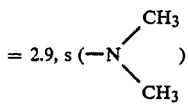 |

2nd step: N,N-dimethyl (3-amino 4-orthochlorophenyl) 2-butene acetamide [(XVII), X=CH₂]

87.5 g of the compound of formula (XVIII) obtained in the preceding step in 250 ml of ethanol are saturated with ammonia, and the mixture is brought up to 80° C. for 5 hours in an autoclave. Then the solvent is evaporated, the crude product is taken up in methylene chloride, washed with water, dried on sodium sulfate, filtered and the filtrate is evaporated. 87 g of the expected product are obtained.

Yield: 98%.

| NMR spectrum | |
|---|---|
| (CDCl₃)δppm | = 7.25, m (benzenic protons) |
| | = 6.55, m (—NH₂) |
| | = 4.7, s |
| | 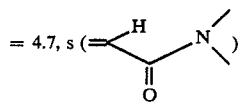 |
| | = 3.6, s 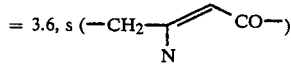 |
| | 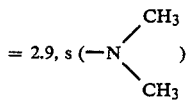 |

3rd step: N,N-dimethyl (3-amino 4-orthochlorophenyl) butanamide [(XVI), X=CH₂]

16 g of sodium borohydride are slowly added to 100 ml of acetic acid. Then a solution of 50 g of preceding compound of formula (XVII) in 150 ml of acetic acid are slowly added and it is left for 5 hours at ambient temperature. Then it is basified with concentrated NaOH (while cooling with ice) and extracted with methylene chloride. It is dried on sodium sulfate, filtered and the filtrate evaporated. Thus 25 g of the desired compound are obtained.

Yield: 50%.

| NMR spectrum | |
|---|---|
| (CDCl₃)δppm | = 7.2, m (benzenic protons) |
| | = 3.6, s (φ-CH₂) |
| | = 2.9, s, 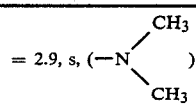 |
| | = 2.85, m 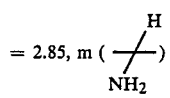 |
| | = 2.45, m, 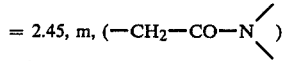 |
| | = 1.7, s, (—NH₂) |

4th step: N,N-dimethyl (3-amino 4-orthochlorophenyl) butanamine [(XV), X=CH₂, n=2]

Code number: 90

To a suspension of 15.8 g of AlLiH₄ in 300 ml of THF are added 50 g of the compound of formula (XVI) obtained in the preceding step (in solution in 200 ml of THF). It is left for 30 minutes at 0° C. then brought to 70° C. for 3 hours. After hydrolysis with wet sodium sulfate, ether is added, it is filtered and the filtrate is evaporated. 40 g of the expected product are obtained.

Yield: 82%.

| NMR spectrum | |
|---|---|
| (CDCl₃)δppm | = 7.2, m (benzenic protons) |
| | = 2.2, s 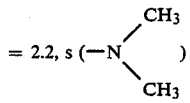 |
| | = 1.9, s (—NH₂) |
| | = 2.2, m 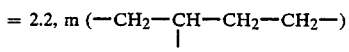 |

5th step: 1-Dimethylamino 3-benzamido 4-orthochlorophenyl butane [(XI), n=2, X=CH₂]

Code number: 57

To a solution cooled to 0° C. of 53.2 g of the compound of formula (XV) obtained in the preceding step in 43 ml of triethylamine and 500 ml of methylene chloride are added 30 ml of benzoyl chloride. It is left 30 mn at 0° C., then 2 hours at ambient temperature. Then it is evaporated, the residue is taken up in ether, washed with water, evaporated and the residue taken up in hydrochloric ethanol and ether, the hydrochloride obtained in filtered and recrystallized from isopropylic acid. Thus the desired compound is obtained with a yield of 50%. Melting point 130° C.

By the processes described in the 4th and 5th steps of example 4, the compound of formula (XI) were obtained, shown under code numbers 56 to 85 and 116 to 120 in table II as well as the compounds of formula (XV) appearing under code numbers 89 to 91, 121 and 122 in table III.

EXAMPLE 5

Phenetylamine α-(3-N,N-dimethylamino propyl) [(XV), X=CH₂, n=3]

Code number: 92

1st step: 2-Benzyl 2-[3-(N,N-dimethylamino 1-propyl] 1,3-dioxolan hydrochloride [(XXII, X=CH$_2$]

To a solution of 12.9 g of LiAlH$_4$ in 300 ml of THF is slowly added a solution of 45 g of 3-[(2-benzyl) 1,3-dioxolan 2-yl] N,N-dimethylpropanamide [(XIXa), X=CH$_2$] in 200 ml of THF. Then the mixture is brought to reflux for 2 hours. After cooling, it is hydrolysed with wet sodium sulfate, diluted in ether, filtered and the filtrate is evaporated. The residue is dissolved in ether. Hydrochloric acid gas is added, the product obtained is filtered and recrystallized from isopropylic alcohol.

Yield: 86%.
Melting point: 194° C.

2nd step: 5-N,N-dimethylamino 1-phenyl pentan 2-one hydrochloride [(XXI), X=CH$_2$]

A solution of 24.6 g of the compound of formula (XXII) obtained in the preceding step in a mixture of 250 ml of acetone and 30 ml of 1 N hydrochloric acid, is stirred for 12 hours. Then, the mixture obtained in neutralized with potassium bicarbonate, filtered, the acetone is evaporated, the residue is taken up in water, extracted with ether, chlorohydric ethanol is added, the formed precipitate is filtered and recrystallized from isopropylic alcohol.

Yield: 88%.
Melting point: 130° C.
Molecular weight: 241.75.
Empirical formula: C$_{13}$H$_{20}$ClNO.
Elementary analysis:

|  | C | H | N |
|---|---|---|---|
| Calculated (%) | 64.58 | 8.34 | 5.79 |
| Obtained (%) | 64.62 | 8.51 | 5.74 |

3rd step: 5-N,N-dimethylamino 1-phenyl pentan 2one oxime [(XX), X=CH$_2$]

A mixture of 87 g of the compound of formula (XXI) obtained in the preceding step in base form, 142 g of sodium bicarbonate and 117.8 of hydroxylamine hydrochloride in a mixture of 500 ml of water and 500 ml of alcohol is left under agitation for 12 hours at ambient temperature. Then it is extracted with methylene chloride, washed with water, dried on sodium sulfate, filtered and the filtrate is evaporated. 90% of oil is obtained which is used in the crude state in the next step.

NMR spectrum (CDCl$_3$)δppm
= 10.8, m (=N—OH)
= 7.22, s (benzenic protons)
= 3.52 and 3.78, s (—φCH$_2$)
= 2.21, m, (CH$_2$—CH$_2$—N(CH$_3$)$_2$)

4th step: Phenetylamineα-(3-N,N-dimethylamino propyl)[(xv), X=CH$_2$, n=3]

To a solution of 21.5 g of AlLiH$_4$ in 300 ml of THF is slowly added a solution of 43.7 g of the compound of formula (XX) obtained in the preceding step in 200 ml of THF. Then the mixture is brought to reflux for 8 hours, cooled, hydrolyzed with wet sodium sulfate, filtered and the filtrate is evaporated. 64% of an oily compound is obtained which is used as it is for the synthesis of the corresponding compound of formula (XI).

NMR spectrum (CDCl$_3$)δppm
= 7.2, m, (benzenic protons)
= 2.18, s (—N(CH$_3$)$_2$)
= between 3.6 and 1.2, m, (CH$_2$—CH(—)CH$_2$)$_3$—)

EXAMPLE 6

N,N-dimethyl 2-[2-(orthochlorobenzyl) 1,3-dioxolan 2-yl] ethyl acetamide ](XIX), X=CH$_2$]

1st step: 2-]2-(orthochlorobenzyl) 1,3-dioxolan -2-yl] ethyl acetate ](XXIV), X=CH$_2$; p=1]

A solution of 48 g of 4-orthochlorophenyl 3-oxo ethyl butanoate [(XXV), X=CH$_2$, p=1] and 3 g of paratoluene sulfonic acid in 33.6 g of ethylene glycol and 600 ml of benzene is brought to reflux for 2 hours, while eliminating the water formed. Then it is washed with water, dried on sodium sulfate, filtered and the filtrate is evaporated. 57 g of the desired compound is obtained.
Yield: 100%.

NMR spectrum (CDCl$_3$)δppm
= 7.2, m (benzenic protons)
= 4.2, q (—COO—CH$_2$)
= 3.7, m, (O—CH$_2$—CH$_2$—O)
= 3.3, s (φ-CH$_2$—)
= 2.6, s (CH$_2$ with dioxolane COO—)

2nd step: [2-(orthochlorophenyl) 1,3-dioxolan[ 2-yl acetic acid [(XXIII), X=CH$_2$, p=1]

A mixture of 110 g of the compound of formula (XXIV) obtained in the preceding step and 32 g of NaOH pellets in 500 ml of ethanol and 500 ml of water is left under agitation for 12 hours at ambient temperature. Then the solvents are evaporated, the residue diluted in water and ethyl ether, the aqueous phase is decanted and acidified with oxalic acid. Then it is extracted with ether, dried on sodium sulfate, filtered and the filtrate is evaporated. 79 g of the desired compound are obtained.
Yield: 80%.

NMR spectrum (CDCl$_3$)δppm
= 9.8, m (—COOH)
= 7.2, m (benzenic protons)
= 3.8, m (O—CH$_2$—CH$_2$—O)

-continued

= 3.3, s (φ-CH$_2$—)
= 2.7, s (—CH$_2$—COOH)

3rd step: N,N-dimethyl 2-[2-(orthochlorobenzyl) 1,3-dioxolan 2-yl] acetamide [(XIX), X=CH$_2$]

To a solution cooled to 0° C. of 96 g of the compound of formula (XXIII) obtained in the preceding step in 800 ml of THF are added 57 ml of triethylamine then 43 ml of ethyl chloroformate. It is left for 1 hour at 0° C. then dimethylamine gas is added. Then the THF is evaporated, the residue is taken up in methylene chloride, washed with 1 N NaOH, then with 1 N hydrochloric acid, then with water, dried on sodium sulfate, filtered and the filtrate evaporated. 96 g of the desired compound are obtained.

Yield: 90%.

NMR spectrum (CDCl$_3$)δppm = 7.3, m, (benzenic protons)

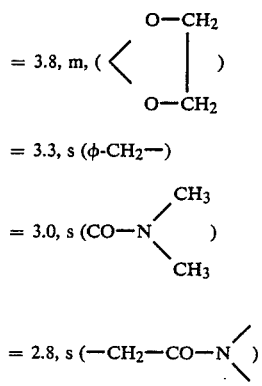

EXAMPLE 7

1-Dimethylamino 2-amino 3-phenoxy propane dioxalate [(XV), X=CH$_2$-O, n=1

Code number: 93

1st step: 1-Dibenzylamino 2-chloro 3-phenoxy propane (XXVII)

To a solution of 675 g of 1-dibenzylamino 3-phenoxy propan 2ol (XXVIII) in 800 ml of methylene chloride are slowly added 296 ml of thionly chloride. Then the solution if brought to reflux for 8 hours, the solvents are evaporated under vacuum, the residue is taken up in methylene chloride, washed with an aqueous solution of sodium bicarbonate, then with water, dried on magnesium sulfate, filtered and the filtrate is evaporated. 700 g (yield: 98%) of the expected compound are obtained, which is oily and used in the crude state in the next step.

2nd step: 1-Dimethylamino 2-dibenzylamino 3-phenoxy propane [(XXVI)]

A solution of 776 g of the compound of formula (XXVII) obtained in the preceding step and 500 of dimethylamine in 2500 ml of ethanol is brought to reflux for 3 hours in an autoclave. Then the solvent and the excess dimethylamine are evaporated, the residue is taken up in methylene chloride, washed with water, dried on magnesium sulfate, filtered, the filtrate is evaporated and the residue distilled.

Yield: 93%.
E$_{0.05}$: 220° C.

3rd step: 1-Dimethylamino 2-amino 3-phenyl propane dioxalate [(XV), X=CH$_2$:O, n=1]

Code number: 93

A suspension of 200 g of dihydrochloride of the preceding compound of formula (XXVI) and 50 g of 10% palladium on charcoal in 500 ml of ethanol is hydrogenolised in an autoclave under hydrogen pressure and at a temperature of 40° to 50° C. After 3 hours of reaction, it is filtered, the filtrate is evaporated, taken up in water, basified with concentrted NaOH, extracted with chloroform, washed with water, dried on sodium sulfate, filtered, the filtrate is evaporated, the residue is dissolved in methanol, an oxalic acid methanol solution is added and the product obtained is filtered.

Yield: 92%.
Melting point: 163° C.
Molecular weight: 374.34.
Empirical formula: C$_{15}$H$_{22}$N$_2$O$_9$.
Elementary analysis:

|  | C | H | N |
|---|---|---|---|
| Calculated (%) | 48.12 | 5.92 | 7.48 |
| Obtained (%) | 48.08 | 5.80 | 7.53 |

EXAMPLE 8

Hydrated 3-(2-amino) ethyl 1-phenyl 3,4-dihydro isoquinoline dioxalate (I)

Code number: 15

1st step: 3-(2-phthalimido) ethyl 1-phenyl 3,4-dihydro isoquinoline [(XXIX), q=2]

A suspension of 10.6 g of potassium phthalimide, 15.1 g of 3-(2-hydroxy) ethyl 1phenyl 3,4-dihydro isoquinoline mesylate (XXX) and 2.9 g of tri n-butyl hexadecyl phosphonium bromide in 100 ml of toluene is brought to 75° C. for 1 hour then to reflux for 2 hours. Then it is washed with water, dried on sodium sulfate, the filtrate is evaporated and the residue recrystallized from ethyl acetate (80%)—hexane (20%). Thus the desired product is isolated.

Yield: 71%.
Melting point 127° C.
Molecular weight: 380.43.
Empirical formula: C$_{25}$H$_{20}$N$_2$O$_2$.
Elementary analysis:

|  | C | H | N |
|---|---|---|---|
| Calculated (%) | 78.92 | 5.30 | 7.36 |
| Obtained (%) | 79.13 | 5.56 | 7.26 |

2nd step: Hydrated 3-(2-amino) ethyl 1-phenyl 3,4-dihydro isoquinoline dioxalate (I)

Code number: 15

A solution of 10 g of preceding compound (XXIX) and 3.3 ml of hydrazine hydrate in 150 ml of alcohol is brought to reflux for 2 hours. Then the solvent is evaporated, the residue is taken up in water and acetic acid while adjusting the pH to 3, cooled to 0° C. and filtered. Then it is acidified with concentrated hydrochloric acid, washed with methylene chloride, basified with concentrated NaOH, extracted with methylene chloride, dried on sodium sulfate, filtered, the filtrate is evaporated, the residue is dissolved in ethyl acetate, a solution of oxalic acid in ethyl acetate is added and the precipitate formed is filtered.

Yield: 67%.
Melting point: 156° C.
Empirical formula: $C_{19}H_{20}N_2O_4 + 1.8\%\ H_2O$.
Elementary analysis:

|  | C | H | N |
|---|---|---|---|
| Calculated (%) | 56.93 | 5.20 | 6.27 |
| Obtained (%) | 56.83 | 5.03 | 6.21 |

By the same process, but from the corresponding reagents, compound (I) was obtained shown as code number 20 in table I.

EXAMPLE 9

3-(2-methylamino) ethyl 1-phenyl 3,4-dihydro isoquinoline dihydrochloride (I)

Code number: 16

A solution of 100 ml of methylamine and 11.7 g of 3-(3-hydroxy) ethyl 1-phenyl 3,4-dihydro isoquinoline mesylate (XXX) in 500 ml of benzene is brought to 40° C. for 12 hours. Then it is washed with water, dried on sodium sulfate, filtered, the filtrate is evaporated, the residue is dissolved in ether, hydrochloric ethanol is added and the precipitate formed is filtered.
Yield: 59%.
Melting point: 145° C.
Molecular weight: 337.29.
Empirical formula: $C_{18}H_{22}Cl_2N_2$.

NMR spectrum ($C_{13}$)
(CDCl$_3$)δppm
= 32.1 and 35 ($-CH_2-CH_2-N\diagup\diagdown$)
= 36 ($-NH-CH_3$)
= 49.4 ($-CH_2-$ in 4)
= 56.1 ($-CH-$ in 3)
= 166.6 ($-C=N-$)
between 138 and 120 (CH and aromatic C)

By the same process but from the corresponding reagents, compound (I) shown as code number 21 in table I is obtained as well as those shown under code numbers 17 to 19, 22 to 39, 86 and 102 to 108 in this same table I.

EXAMPLE 10: 3-(2-hydroxy) ethyl 1-phenyl 3,4-dihydro isoquinoline mesylate [(XXX), q=2]

1st step: N-(3-hydroxy 1-benzyl) propyl benzamide [(XXXIV), q=2]

To a suspension of 6 g of AlLiH$_4$ in 250 ml of THF is slowly added a solution of 49 g of 3-benzoylamino 3-benzyl propionic acid ethyl ester (XXXV) in 250 ml of THF. It is left under agitation for 4 hours at 0° C., then it is neutralized with wet sodium sulfate, diluted with ester, filtered, the filtrate is evaporated and the residue crystallized in ethyl acetate. Thus, 38 g of the desired product are isolated.
Yield: 90%.
Melting point: 108° C.

2nd step: N-(3-acetyloxy 1-benzyl) propylbenzamide [(XXXIII, q=2]

To a solution cooled to 0° C. of 38 g of the compound of formula (XXXIV) obtained in the preceding step in 400 ml of pyridine are added 50 ml of acetic anhydride. After 12 hours at ambient temperature, the solvent is evaporated, the residue is taken up in methylene chloride, washed with water, dried on sodium sulfate, filtered, the filtrate is evaporated and the residue recrystallized in acetic acid. 36 g of the desired product are isolated.
Yield: 82%.
Melting point: 120° C.

3rd step: 3-(2-acetyloxy) ethyl 1-phenyl 3,4-dihydro isoquinoline [(XXXII), q=2]

A solution of 59 g of the compound of formula (XXXIII) obtained in the preceding step in 500 ml of phosphorous oxychloride is brought for 30 mn to 110° C. Then it is left for 3 hours at 80° C. It is evaporated and the residue is taken up in water and ice, washed with ether, basified with concentrated NaOH, extracted with methylene chloride, washed in water, dried on sodium sulfate, filtered, the filtrate is evaporated and the residue chromatographed on an alumina column (eluent: ether). 22 g of an oily compound are obtained.
Yield: 40%

NMR spectrum = 7.4, m (9 benzenic protons)
(CDCL$_3$) δ ppm
= 4.45, t, ($-CH_2-OCO-$)
= 3.6, m, (H at 3)
= 2.65, m, (CH$_2$ at 4)
= 2.1, m, ($-CH_2-CH_2-OCO-CH_3$)

By the same process, but from the corresponding reagents, there was obtained:
3-(2-acetyloxy) ethyl 7-methoxy 1-phenyl 3,4-dihydro isoquinoline [(XXXII), q=2] (oil) - NMR spectrum (CDCl$_3$) δppm=6.8 to 7.8, m (8 aromatic H); 4.4, t (CH$_2$-OCO); 3.7, s (CH$_3$O); 3.4 to 3.8, m (H at 3); 2.7, m (H at 4); 2.05, s (CH$_3$CO); 2, m (CH$_2$); and
3-(2-acetyloxy) ethyl 7-methyl 1-phenyl 3,4-dihydro isoquinoline [(XXXII), q+2] (oil) NMR spectrum (CDCl$_3$) δppm=7 to 8, m (8 aromatic H); 4.4, t (CH$_2$OCO); 3.6, m (H at 3); 2.65, m (H at 4); 2.3, s (CH$_3$); 2.05, s (CH$_3$CO); 2, m (CH$_2$).

4th step: 3-(2-hydroxy) ethyl 1-phenyl 3,4-dihydro isoquinoline hydrochloride [(XXXI), q=2]

A suspension of 21.8 g of the compound of formula (XXXII) obtained in the preceding step and 3 g of potassium carbonate in 250 ml of methanol is left for 12 hours at ambient temperature. Then it is filtered, the filtrate is evaporated, the residue is dissolved in ether, hydrochloric ethanol is added and the precipitate obtained is filtered. 16 g of product are obtained.
Yield: 89%.
Melting point: 200° C.
Molecular weight: 287.78.
Empirical formula: $C_{17}H_{18}ClNO$.
Elementary analysis:

|  | C | H | N |
|---|---|---|---|
| Calculated (%) | 70.95 | 6.30 | 4.87 |
| Obtained (%) | 70.75 | 6.35 | 4.63 |

By the same process, but from the corresponding reagents, there are obtained:
3-(2-hydroxy) ethyl7-methoxy 1-phenyl 3,4-dihydro isoquinoline [(XXXI), q=2] (oil); NMR spectrum (CDCl$_3$) δppm=6.8 to 7.8, m (8 aromatic H); 5.3, s (OH); 4, t (CH$_2$O); 3.7, s (CH$_3$O); 3.7 m (H at 3); 2.5 to 2.8, m (H at 4); 2, m (CH$_2$); and 3-(2-hydroxy) ethyl 7-methyl 1-phenyl 3,4-dihydro isoquinoline [(XXXI), q=2] (oil); NMR spectrum (CDCl$_3$) δppm=7 to 7.6, m (8 aromatic H); 3.92, t (C$\underline{H}_2$O); 3.5, m (H at 3); 2.2, s (C$\underline{H}_3$); 2.5 to 2.8, m (H at $\overline{4}$); 1.95, m (C$\underline{H}_2$).

5th step: 3-(2-hydroxy) ethyl 1-phenyl 3,4-dihydro isoquinoline mesylate (XXX)

To a solution cooled to −10° C. of 9 g of the compound of formula (XXXI) obtained in the preceding step and 12.5 ml of triethylamine in 250 ml of methylene chloride are added 5.4 ml of mesyl chloride. Then it is left for 30 minutes at ambient temperature, then washed with water with the help of 1 N hydrochloric acid solution, with water, with a sodium bicarbonate solution, dired on sodium sulfate, filtrated and the filtrate is evaporated. An oil is obtained which is then crystallized.

Yield: 89%.
Melting point: 94° C.

EXAMPLE 11

3-(2-N,N-dimethylamino) ethyl 3,4-dihydro 1-orothofluorophenyl naphthalene maleate (I)

Code number: 101

1st step: 3-(2-hydroxy) ethyl 1,2,3,4 tetrahydro naphthalene 1-one [(X); n=2]

A solution of 28.3 g of 2-(1,2,3,4-tetrahydro naphthalene 1-one 3-yl) acetic acid (VIII) in 150 ml of ethanol, 30 ml of 7 N hydrochloric ethanol and 150 ml of benzene is brought to reflux for 8 hours. Then the solvents are evaporated, the residue is taken up in ether, washed with water, dried on sodium sulfate, filtered and the filtrate evaporated. 38 g (Yield ~100%) of 2-(1,2,3,4-tetrahydro napathalene 1-one 3-yl) acetic acid ethyl ester are obtained, the NMR spectrum of which has the following characteristics: δppm=7.8 to 8.1, m (aromatic H at 8); 7.2 to 7.6, m (aromatic H at 5, 6 and 7); 4.15, q (COO—C$\underline{H}_2$); 2.4 to 3, m (7 H: protons at 2,3,4 and C$\underline{H}_2$—CO—O—); 1.25, t (C$\underline{H}_3$).

25.2 g of this ester are dissolved in 250 ml of methylene chloride and 14.7 ml of ethane dithiol and 5 ml of boron trifluoride etherate are added, it is left for 36 hours at ambient temperature, then 350 ml of 1 N NaOH are added, the organic phase is decanted, washed with water, dried on sodium sulfate, filtered, the filtrate is evaporated and the residue chromatographed on an alumina column. By elution with a cyclohexane (90%) - ethyl acetate (10%) mixture, 26.8 g (yield: 83%) of 2-[3-éthoxycarbonylmetnhyl 1,2,3,4-tetrahydro 1-yl] 1,3-dithiolan; NMR spectrum (CDCl$_3$) δppm=7.9 to 8.1, m (aromatic H at 8); 6.9 to 7.3, m (aromatic H at 5, 6 and 7); 4.2, q (—COO—C$\underline{H}_2$); 3.4 to 3.6,

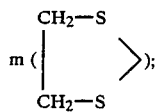

2.4 to 2.8, m (protons at 2,3,4 and C$\underline{H}_2$—CO—O); 1.35, t (CH$_3$), are obtained.

This compound is added to a suspension cooled at 0° C. of 3.5 g of lithium aluminium hydride in 250 ml of THF. It is left at 0° C. for 3 hours, then hydrolyzed with wet sodium sulfate, filtered and the filtrate is evaporated. 24 g (Yield=99%) of 2-[3-(2-hydroxy ethyl 1,2,3,4-tetrahydro 1-yl] 1,3-dithiolan NMR spectrum (CDCl$_3$) δppm=7.8 to 8, m (aromatic H at 8); 6.8 to 7.3, m (aromatic H at 5,6 and 7); 3.6,

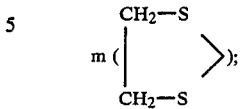

1.4 to 3, m (protons at 2,3,4 and —C$\underline{H}_2$—C$\underline{H}_2$—OH), are obtained.

The preceding alcohol is dissolved in a solution of 300 ml of methanol (containing 5% of water) and 50 ml of methyl iodide. The mixture is brought to reflux for 12 hours, then the solvents are evaporated, the residue is taken up in ether, washed with water, dried on sodium sulfate, filtered, the filtrate is evaporated and the residue is chromatographed on a silica column. By elution with the methyl chloride (89%) - methanol (10%) - ammonia (1%) mixture, 36 g (Yield=79%) of the expected compound (oily, were obtained.

NMR spectrum (CDCl$_3$) δppm=7.8 to 8.2, m (aromatic H at 8); 7.2 to 7.6, m (aromatic H at 5, 6 and 7); 3.8, t (C$\underline{H}_2$—OH); 2.2 to 3, m (H at 2,3,4 and —O$\underline{H}$); 1.6 to 1.9,

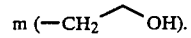

2nd step: tertiobutyl dimethyl silyl ether of 3-(2-hydroxy)ethyl 1,2,3,4-tetrahydro naphthalene 1-one (IX).

A mixture of 4.5 g of compound (X) obtained in the preceding step, 4.03 g of imidazol and 4.3 g of tertiobutyl dimethyl silyl chloride is left under agitation at ambient temperature for 12 hours. Then it is diluted with water, extracted with ethyl acetate, dried on sodium sulfate, filtered and the filtrate is evaporated, the residue is taken up in ether and washed with a 5% solution of potassium acid sulfate, then with a sodium chloride solution. After drying on sodium sulfate, it is filtered and the filtrate evaporated. 7 g (Yield=97%) of the expected product (oily) are obtained.

NMR spectrum (CDCl$_3$) δppm=8.1, m (1 aromatic H at 8); 7.35 to 7.6, m (aromatic H at 5,6 and 7); 3.82, t (C$\underline{H}_2$—O—); 2.4 to 3.1, m (H at 2, 3 and 4); 1.7,

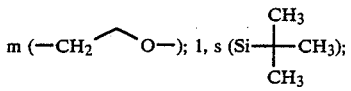

0.2, s (CH$_3$—Si—CH$_3$).

3rd step: 3-(2-hydroxy ethyl) 3,4-dihydro 1-orthofluorophenyl naphthalene (IV)

To a solution cooled to −93° C. of 11.7 ml of a 2.4 M butyl lithium hexane solution in 20 ml of ether in a stream of argon are slowly added 3.2 ml of 1-bromo 2-fluoro benzene. It is left for 30 minutes at −93° C., then in 11 minutes is added a solution of 3 g of compound (IX) obtained in the preceding step in 50 ml of ether. After 2 hours at −80° C., 10 ml of hydrochloric ethanol are added, the solents are evaporated, the residue is taken up in ether, washed in water, dried on sodium sulfate, filtrated, the filtrate is evaporated and the residue chromatographed on a silica column. By elution with the ether (70%) - heptane (30%) mixture, 1.3 g (Yield=50%) of the expected product (oily) are obtained.

NMR spctrum (CDCl$_3$) δppm=7.6 to 7.4, m (aromatic H at 8); 5.95,

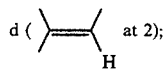

3.7, t (C$\underline{H}_2$—OH); 2.4 to 3, m (H at 3 and 4 and —O$\underline{H}$); 1.7,

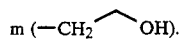

4th step: 3-(2-N,N-dimethylamino) ethyl 3,4-dihydro 1-orthofluorophenyl naphthalene maleate (I)

Code number: 101

To a solution of 1.2 g of compound (IV) obtained in the preceding step in 30 ml of methylene chloride are added 1.65 ml of triethylamine and 0.75 ml of mesyl chloride. It is left for one hour at ambient temperature, then is diluted with water, the organic phase is decanted, washed with a 1N hydrochloric acid solution, then with water, then with a sodium bicarbonate solution, dried on sodium sulfate, filtered and the filtrate is evaporated. The crude product obtained (1.5 g; yield=93%) is dissolved in 33 ml of a 1.9 M dimethylamine benzene solution, and the mixture is brought to 40° C. for 17 hours in an autoclave. Then the solvent is evaporated, and the residue is taken up in methylene chloride, washed with water, dried on sodium sulfate, filtered, the filtrate is evaporated and the residue chromatographed on a silica column. By elution with the methylene chloride (90%) - ethaol (9.5%) - ammonia (0.5%), 0.61 g (yield=50%) of an oily product is obtained which is dissolved in acetone. An acetone solution of 0.24 g of maleic acid is added, diluted with ether and the precipitate obtained is filtered, which corresponds to the expected product (0.62 g).

Melting point: 134° C.
Molecular weight: 411.46.
Empirical formula: C$_{24}$H$_{26}$FNO$_4$.
Elementary analysis:

|  | C | H | N |
|---|---|---|---|
| Calculated (%) | 70.05 | 6.37 | 3.40 |
| Obtained (%) | 70.15 | 6.74 | 3.47 |

By the same process, but from the corresponding reagents, compound (I) is obtained shown under code number 123 in table I below.

EXAMPLE 12

3-(3-hydroxy propyl) 3,4-dihydro 1-orthofluorophenyl naphthalene [(IV); n=3]

1st step: 3-(2-cyano ethyl) 3,4-dihydro 1-orthofluorophenyl naphthalene (XXXVII)

To a solution of 17.2 g of 3-(2-hydroxy ethyl) 3,4-dihydro 1-orthofluorophenyl naphthalene [(IV), n=2] obtained in example 11 above in 200 ml of methylene chloride, cooled to −10° C., are added 22.3 ml of triethylamine then 10 ml of mesyl chloride. It is left at −10° C., and when the reaction is finished (checked by T.L.C.), it is diluted with water, washed with a dilute hydrochloric solution, then with water, then with a dilute sodium bicarbonate solution, then with water, dried on magnesium sulfate, filtered and the filtrate is evaporated. The crude product (22.2 g) is dissolved in 100 ml of DMSO and 25 g of sodium cyanide are added. The mixture is left for a night at ambient temperature, then diluted with water, extracted with chloroform, washed with water, dried on magnesium sulfate, filtered and the filtrate is evaporated. 18 g of the expected product (oily) are obtained.

IR spectrum (microcell) CN band at 2240 cm$^{-1}$.

2nd step: 3-(2-ethoxycarbonyl ethyl) 3,4-dihydro 1-orthofluorophenylnaphthalene (XXXVI)

A solution of 18 g of the preceding compound (XXXVII) in 200 ml of ~7 N hydrochloric ethanol and 200 ml of ethanol is brought to reflux for 36 hours. Then the solvent is evaporated, the residue is taken up in methylene chloride, washed with a sodium bicarbonate solution, then with water, dried on magnesium sulfate, filtered and the filtrate is evaporated. 15 g of expected compound are obtained in the form of oil.

IR spectrum (microcell) band COOEt at 1730 cm$^{-1}$.

NMR spectrum (CDCl$_3$)δppm=6.8 to 7.8, m (8 aromatic protons), 5.92, d (H at 2), 4.1, q (—COOC$\underline{H}_2$), 1.22, t (—COO⌢CH$_3$)

2.2 to 3.1, m (C$\underline{H}_2$—COO and H at 3 and 4), 1.8, m (C$\underline{H}_2$).

3rd step: 3-(3(hydroxy propyl) 3.4-dihydro 1-orthofluorophenyl naphthalene [(IV), n=3]

To a suspension of 1.7 g of lithium aluminium hydride in 50 ml of THF, cooled to 0° C., is added in 5 mn a solution of 14.8 g of compound (XXXVI), previously obtained, in 100 ml of THF. Then after 1 hour, it is hydrolized with wet sodium sulfate diluted with ether, filtered, the filtrate is evaporated and the residue chromatographed on a silica column. By elution with the heptane (60%) - ethyl acetate (40%), 12.1 g of the expected compound (oily) are obtained:

NMR spectrum (CDCl$_3$) δppm=6.7 to 7.8, m (8 aromatic H), 6, d (H at 2), 3.6, m (C$\underline{H}_2$—OH), 2.42, s (—O$\underline{H}$), 2.6 to 3.1, m (H at 3 and $\overline{4}$), 1.6, m (—C$\underline{H}_2$—C$\underline{H}_2$—).

TABLE I

(I)

| Code Number | A | X | R | R$_1$N-R$_2$ | n | R$_3$ | Form | Empirical Formula | Molecular Weight | Melting point (°C.) | | ELEMENTARY ANALYSIS (or NMR spectrum) % | | |
|---|---|---|---|---|---|---|---|---|---|---|---|---|---|---|
| | | | | | | | | | | | | C | H | N |
| 1 | CH | CH$_2$ |  | -N(CH$_3$)(CH$_3$) | 1 | H | Oxalate | C$_{19}$H$_{23}$NO$_4$ | 353.40 | 100 | Cal. Obt. | 71.37 71.44 | 6.56 6.55 | 3.96 3.82 |
| 2 | " | " | " | -N(CH$_3$)(CH$_3$) | 2 | " | Oxalate + 0.62% H$_2$O | C$_{22}$H$_{25}$NO$_4$ + 0.62% H$_2$O | 369.72 | 162 | Cal. Obt. | 71.46 71.40 | 6.89 6.57 | 3.79 3.45 |
| 6 | N | CH$_2$ |  | -N(CH$_3$)(CH$_3$) | 1 | H | Base | C$_{18}$H$_2$ON$_2$ | 264.35 | 68 | Cal. Obt. | 81.78 81.84 | 7.63 7.88 | 10.60 10.62 |
| 7 | " | " | " | -N(piperazine-N—CH$_3$) | " | " | Base + 3/5 H$_2$O | C$_{21}$H$_{25}$N$_3$ + 3/5 H$_2$O | 330.24 | 107 | Cal. Obt. | 76.37 76.52 | 8.00 8.22 | 12.73 12.98 |
| 8 | " | " |  | -N(CH$_3$)(CH$_3$) | " | " | Oxalate | C$_{20}$H$_{21}$FN$_2$O$_4$ | 372.38 | 200 | Cal. Obt. | 64.50 64.30 | 5.68 5.99 | 7.52 7.54 |
| 9 | N | CH$_2$ |  | -N(CH$_3$)(CH$_3$) | 1 | 7-Cl | diHCl + H$_2$O | C$_{18}$H$_{20}$Cl$_3$N$_2$ + H$_2$O | 407.74 | 150 | Cal. Obt. | 53.02 53.18 | 5.44 5.48 | 6.87 6.76 |

TABLE I-continued $$\begin{array}{c} R_1 \\ R_2 \end{array}\!\!N\!-\!(CH_2)_n \overset{R}{\underset{A}{\diagdown}}\!\!\begin{array}{c} \\ \diagup \\ X \end{array}\!\!\!\begin{array}{c} R_3 \\ \end{array} \qquad (I)$$

| Code Number | A | X | R | n | $\begin{array}{c}R_1\\ \diagdown\\ N\\ \diagup\\ R_2\end{array}$ | R₃ | Form | Empirical Formula | Molecular Weight | Melting point (°C) | | ELEMENTARY ANALYSIS (or NMR spectrum) % | | |
|---|---|---|---|---|---|---|---|---|---|---|---|---|---|---|
| | | | | | | | | | | | | C | H | N |
| 10 | " | " | phenyl | " | $\begin{array}{c}\diagdown\\ N\\ \diagup\end{array}$ | 7-F | Base | C₁₈H₁₉FN₂ | 282.35 | 98 | Cal. Obt. | 76.57 76.53 | 6.78 6.81 | 9.92 9.90 |
| 11 | " | " | " | " | CH₃ \ N / CH₃ | 7-Cl | Base | C₁₈H₁₉ClN₂ | 298.81 | 100 | Cal. Obt. | 72.35 71.99 | 6.41 6.65 | 9.38 9.22 |
| 12 | " | " | " | " | " | 7-CH₃ | " | C₁₉H₂₂N₂ | 278.38 | 90 | Cal. Obt. | 81.97 82.07 | 7.97 8.19 | 10.06 9.79 |
| 13 | N | CH₂ | phenyl | 1 | CH₃ \ N / CH₃ | 7-OCH₃ | di HCl + ½ H₂O | C₁₉H₂₄Cl₂N₂O + ½ H₂O | 376.32 | 202 | Cal. Obt. | 62.12 61.63 | 6.59 6.67 | 7.63 7.44 |
| 14 | " | " | " | " | " | 6,7-diOCH₃ | Base | C₂₀H₂₄N₂O₂ | 324.41 | 135 | Cal. Obt. | 74.04 74.22 | 7.46 7.59 | 8.64 8.69 |
| 15 | " | " | " | 2 | —NH₂ | H | Oxalate + 1.8% H₂O | C₁₉H₂₀N₂O₄ + 1.8% H₂O | 447.24 | 156 | Cal. Obt. | 56.93 56.83 | 5.20 5.03 | 6.27 6.21 |
| 16 | " | " | " | " | —NHCH₃ | " | diHCl | C₁₈H₂₂Cl₂N₂ | 337.29 | 145 | NMR spectrum C₁₃(CDCl₃) | | | |

δppm = 32.1 and 35 (—CH₂—CH₂—N$\diagup\diagdown$); 36 (—NH—CH₃); 49.4 (—CH₂ in 4); 56.1 (—CH— in 3); 166.6 (—C=N); 120 to 138 (CH and aromatic C)

TABLE I-continued $$\begin{array}{c} R_1 \\ | \\ N-(CH_2)_n \\ | \\ R_2 \end{array} \quad \begin{array}{c} R \\ \diagup \\ A \end{array} \begin{array}{c} \\ \diagdown \\ X \end{array} \begin{array}{c} \\ \\ \end{array} R_3 \quad (I)$$

| Code Number | A | X | R | n | $R_1$ $\diagdown$ N $\diagup$ $R_2$ | $R_3$ | Form | Empirical Formula | Molecular Weight | Melting point (°C.) | % | ELEMENTARY ANALYSIS (or NMR spectrum) C | H | N |
|---|---|---|---|---|---|---|---|---|---|---|---|---|---|---|
| 21 | N | $CH_2$ | 2-F-phenyl | 2 | —$NHCH_3$ | H | Oxalate + 0.6% $H_2O$ | $C_{20}H_{21}FN_2O_4$ + 0.6% $H_2O$ | 374.63 | 188 | Cal. Obt. | 64.11 63.88 | 5.71 5.55 | 7.47 7.39 |
| 22 | " | " | " | " | $CH_3$ $\diagdown$ N $\diagup$ $CH_3$ | " | diHCl + 9/8 $H_2O$ | $C_{19}H_{23}Cl_2FN_2$ + 9/8 $H_2O$ | 389.57 | 140 | Cal. Obt. | 58.57 58.82 | 6.53 6.27 | 7.19 7.12 |
| 23 | " | " | 3-F-phenyl | " | " | " | 1,25 HCl + 4% $H_2O$ | $C_{19}H_{21}FN_2$ + 1.25 HCl + 4% $H_2O$ | 356.20 | 130 | Cal. Obt. | 64.06 64.16 | 6.75 6.80 | 7.87 7.91 |
| 24 | " | " | 4-F-phenyl | " | " | " | diHCl + $H_2O$ | $C_{19}H_{23}Cl_2FN_2$ + $H_2O$ | 389.32 | 194 | Cal. Obt. | 58.61 58.69 | 6.79 6.67 | 7.20 7.03 |
| 25 | N | $CH_2$ | 2-Cl-phenyl | 2 | $CH_3$ $\diagdown$ N $\diagup$ $CH_3$ | H | Oxalate + ¼ $H_2O$ | $C_{21}H_{23}ClN_2O_4$ + ¼ $H_2O$ | 407.37 | 146 | Cal. Obt. | 61.91 62.04 | 5.81 5.70 | 6.88 6.89 |

TABLE I-continued $$\begin{array}{c} R \\ | \\ A \\ | \\ \end{array} \underset{R_1 \quad R_2}{\overset{R_3}{\underset{N-(CH_2)_n}{\bigcirc}}} \quad (I)$$

| Code Number | A | X | R | n | $\underset{R_2}{\overset{R_1}{\diagdown}}N-$ | R₃ | Form | Empirical Formula | Molecular Weight | Melting point (°C.) | | ELEMENTARY ANALYSIS (or NMR spectrum) % | | |
|---|---|---|---|---|---|---|---|---|---|---|---|---|---|---|
| | | | | | | | | | | | | C | H | N |
| 26 | " | " | 3-Cl-phenyl | " | " | " | Oxalate | C₂₁H₂₃ClN₂O₄ | 411.87 | 155 | Cal. Obt. | 61.82 61.55 | 5.68 5.84 | 6.80 6.53 |
| 27 | " | " | 4-Cl-phenyl | " | " | " | diHCl + 0.9 H₂O | C₁₉H₂₃Cl₃N₂ + 0.9 H₂O | 401.97 | 210 | Cal. Obt. | 56.77 56.60 | 6.22 5.92 | 6.97 6.70 |
| 28 | " | " | 2-OMe-phenyl | " | " | " | 1.5 HCl + 6.2% H₂O | C₂₀H₂₄N₂O + 1.5 HCl + 6.2% H₂O | 387.11 | 145 | Cal. Obt. | 62.05 61.79 | 7.33 6.95 | 7.24 7.30 |
| 29 | N | CH₂ | 3-OMe-phenyl | 2 | $\underset{CH_3}{\overset{CH_3}{\diagdown}}N-$ | H | dioxalate | C₂₄H₂₈N₂O₉ | 488.48 | 162 | Cal. Obt. | 59.01 59.24 | 5.78 5.71 | 5.74 5.52 |
| 30 | " | " | 4-OMe-phenyl | " | " | " | diHCl + 4% H₂O | C₂₀H₂₆Cl₂N₂O + 4% H₂O | 397.23 | 200 | Cal. Obt. | 60.47 60.43 | 7.05 6.59 | 7.06 7.02 |

TABLE I-continued

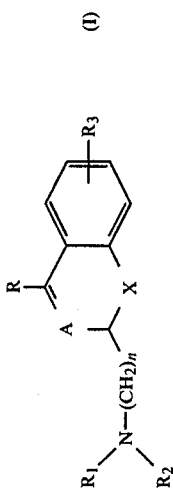

(I)

| Code Number | A | X | R | n | $R_1$ $\diagdown$N$\diagup$ $R_2$ | $R_3$ | Form | Empirical Formula | Molecular Weight | Melting point (°C.) | % | ELEMENTARY ANALYSIS (or NMR spectrum) | | |
|---|---|---|---|---|---|---|---|---|---|---|---|---|---|---|
| | | | | | | | | | | | | C | H | N |
| 31 | " | " | 2-CH$_3$-phenyl | " | " | " | dioxalate + 1.8% H$_2$O | C$_{24}$H$_{28}$N$_2$O$_8$ + 1.8% H$_2$O | 481.14 | 92 | Cal. Obt. | 59.91 60.02 | 6.06 5.86 | 5.82 5.82 |
| 32 | " | " | 3-CH$_3$-phenyl | " | " | " | dioxalate | C$_{24}$H$_{28}$N$_2$O$_8$ | 472.48 | 158 | Cal. Obt. | 61.01 61.17 | 5.97 5.95 | 5.93 5.84 |
| 33 | N | CH$_2$ | 4-CH$_3$-phenyl | 2 | CH$_3$$\diagdown$N$\diagup$CH$_3$ | H | diHCl + H$_2$O | C$_{20}$H$_{26}$Cl$_2$N$_2$ + H$_2$O | 383.35 | 220 | Cal. Obt. | 62.66 62.65 | 7.63 7.63 | 7.31 6.99 |
| 34 | " | " | 2-NO$_2$-phenyl | " | " | " | Oxalate + 0.3 H$_2$O | C$_{21}$H$_{23}$N$_3$O$_6$ + 0.3 H$_2$O | 418.82 | 170 | Cal. Obt. | 60.22 60.49 | 5.68 5.73 | 10.03 9.90 |
| 35 | " | " | 4-NO$_2$-phenyl | " | " | " | diHCl + ⅔ H$_2$O | C$_{19}$H$_{23}$Cl$_2$N$_3$O$_2$ + ⅔ H$_2$O | 408.32 | 185 | Cal. Obt. | 55.88 55.74 | 6.01 5.99 | 10.29 10.06 |

TABLE I-continued $$\underset{R_2}{\overset{R_1}{N}}-(CH_2)_n\underset{A}{\overset{R}{\diagdown}}\underset{}{\diagup}\underset{}{\overset{}{\bigcirc}}-R_3 \quad (I)$$

| Code Number | A | X | R | n | $\underset{R_2}{\overset{R_1}{N}}-$ | $R_3$ | Form | Empirical Formula | Molecular Weight | Melting point (°C.) | | ELEMENTARY ANALYSIS (or NMR spectrum) C H N | | |
|---|---|---|---|---|---|---|---|---|---|---|---|---|---|---|
| | | | | | | | | | | | % | C | H | N |
| 36 | " | " | 2-Br-methylphenyl | " | " | " | diHCl | $C_{19}H_{23}BrCl_2N_2$ | 430.21 | 190 | NMR spectrum $C_{13}$ δppm = 27.5 and 30 ($CH_2-CH_2-N\diagdown{CH_3 \atop CH_3}$)44.($-N\diagdown{CH_3 \atop CH_3}$) 52 ($CH_2$ in 4); 54.5 ($-CH$ in 3) 121 to 139.5 ($-C=N$ and aromatic C and CH) | | | |
| 37 | N | $CH_2$ | cyclohexyl | 2 | $\underset{CH_3}{\overset{CH_3}{N}}-$ | H | diHCl + 1.5 $H_2O$ | $C_{19}H_{30}Cl_2N_2$ + 1.5 $H_2O$ | 384.38 | 140 | Cal. Obt. | 59.37 59.23 | 8.65 8.95 | 7.29 7.23 |
| 38 | " | " | phenyl | 3 | " | " | Dioxalate + 0.15 oxalate | $C_{24}H_{28}N_2O_8$ + 0.15 oxalate | 485.98 | 163 | Cal. Obt. | 60.05 59.90 | 5.87 5.78 | 5.76 5.60 |
| 39 | " | " | 2-F-methylphenyl | " | " | " | 2.2 oxalate | $C_{24}H_{27}FN_2O_8$ + 0.2 oxalate | 508.48 | 138 | Cal. Obt. | 57.63 57.55 | 5.43 5.35 | 5.51 5.65 |
| 40 | " | $CH_2O$ | phenyl | 1 | " | " | HCl | $C_{18}H_{21}ClN_2O$ H + 1/6 $H_2O$ | 319.82 | 163 | Cal. Obt. | 67.59 67.14 | 6.72 6.83 | 8.76 8.67 |

TABLE I-continued (I structure shown with R, R₃ on benzene, A-X-(CH₂)n-N(R₁)(R₂))

| Code Number | A | X | R | n | $\underset{R_2}{\overset{R_1}{N-}}$ | R₃ | Form | Empirical Formula | Molecular Weight | Melting point (°C.) | % | ELEMENTARY ANALYSIS (or NMR spectrum) C | H | N |
|---|---|---|---|---|---|---|---|---|---|---|---|---|---|---|
| 41 | N | CH₂O | 2-F-phenyl | 1 | -N(CH₃)(CH₃) | H | HCl | C₁₈H₂₀ClFN₂O | 334.81 | 216 | Cal. Obt. | 64.57 64.42 | 6.02 6.05 | 8.37 8.48 |
| 42 | " | " | 2-Cl-phenyl | " | " | " | HCl + 0.18 H₂O | C₁₈H₂₀Cl₂N₂O + 0.18 H₂O | 354.51 | 210 | Cal. Obt. | 60.97 61.05 | 5.79 5.80 | 7.90 8.02 |
| 43 | " | " | 3-Cl-phenyl | " | " | " | HCl + 1.3% H₂O | C₁₈H₂₀Cl₂N₂O + 1.3% H₂O | 355.89 | 212 | Cal. Obt. | 60.74 60.81 | 5.82 5.69 | 7.88 7.90 |
| 44 | " | " | 4-Cl-phenyl | " | " | " | 1.15 HCl + 0.8% H₂O | C₁₈H₂₀ClN₂O + 1.15 HCl + 0.8% H₂O | 359.62 | 218 | Cal. Obt. | 60.12 60.20 | 5.73 5.89 | 7.79 7.84 |
| 45 | N | CH₂O | phenyl | 2 | -N(CH₃)(CH₃) | H | diHCl + 3.4% H₂O | C₁₉H₂₄Cl₂N₂O + 3.4% H₂O | 380.24 | 190 | Cal. Obt. | 60.01 60.23 | 6.75 6.78 | 7.37 7.56 |
| 86 | N | CH₂ | 2-pyridyl | 2 | " | " | diHCl + 1.3% H₂O | C₁₈H₂₃Cl₂N₃ + 1.3% H₂O | 356.94 | 110 | Cal. Obt. | 60.56 60.71 | 6.64 6.64 | 11.77 12.04 |

TABLE I-continued $$\begin{array}{c}R_1\\R_2\end{array}N-(CH_2)_n\diagdown\begin{array}{c}R\\A\end{array}\diagup X\diagdown\begin{array}{c}\\ \\ \end{array}R_3 \quad (I)$$

| Code Number | A | X | R | n | $\begin{array}{c}R_1\\ \diagdown\\-N\\ \diagup\\R_2\end{array}$ | $R_3$ | Form | Empirical Formula | Molecular Weight | Melting point (°C.) | | ELEMENTARY ANALYSIS (or NMR spectrum) | | |
|---|---|---|---|---|---|---|---|---|---|---|---|---|---|
| | | | | | | | | | | % | C | H | N |
| 87 | N | CH$_2$O | 3-F-phenyl | 1 | N(CH$_3$)$_2$ | " | 1.5 HCl + 2.4% H$_2$O | C$_{18}$H$_{19}$FN$_2$O + 1.5 HCl + 2.4% H$_2$O | 361.73 | 195 | Cal. Obt. | 59.76 59.44 | 5.97 5.85 | 7.75 7.60 |
| 88 | N | CH$_2$O | 4-F-phenyl | 1 | N(CH$_3$)$_2$ | H | HCl + 0.9% H$_2$O | C$_{18}$H$_{20}$ClFN$_2$O + 0.9% H$_2$O | 337.85 | 210 | Cal. Obt. | 63.99 63.79 | 6.07 6.05 | 8.29 8.30 |
| 94 | " | CH$_2$ | phenyl | " | piperazine-NCH$_3$ | 5-Cl | dimaleate | C$_{29}$H$_{32}$ClN$_3$O$_8$ | 586.03 | 209 | Cal. Obt. | 59.43 58.93 | 5.50 5.52 | 7.17 7.28 |
| 95 | " | " | " | " | N(Et)$_2$ | 7-CH$_3$ | " | C$_{29}$H$_{34}$N$_2$O$_8$ | 538.58 | 114 | Cal. Obt. | 65.67 64.43 | 6.36 6.41 | 5.20 5.23 |
| 96 | " | " | " | " | pyrrolidine | " | " | C$_{29}$H$_{32}$N$_2$O$_8$ | 536.56 | 134 | Cal. Obt. | 64.91 64.71 | 6.01 6.01 | 5.22 5.12 |
| 97 | N | CH$_2$ | phenyl | 1 | piperidine | 7-CH$_3$ | diHCl | C$_{22}$H$_{28}$Cl$_2$N$_2$ | 391.37 | 190 | Cal. Obt. | 67.51 67.34 | 7.21 7.25 | 7.16 7.25 |

TABLE I-continued (I) Structure: R-C(A)-Ar(R3) with X-CH-N(R1)(R2) via (CH2)n chain

| Code Number | A | X | R | n | $\begin{matrix}R_1\\ \diagdown N- \\ R_2\end{matrix}$ | $R_3$ | Form | Empirical Formula | Molecular Weight | Melting point (°C.) | % | ELEMENTARY ANALYSIS (or NMR spectrum) C | H | N |
|---|---|---|---|---|---|---|---|---|---|---|---|---|---|
| 98 | " | " | " | " | morpholine (N-O ring) | " | " | $C_{21}H_{26}Cl_2N_2O$ | 393.35 | 215 | Cal. Obt. | 64.12 64.36 | 6.66 6.86 | 7.12 7.11 |
| 99 | " | " | " | " | 4-methylpiperazine (N—NCH₃) | " | diMaleate | $C_{30}H_{35}N_3O_8$ | 565.60 | 170 | Cal. Obt. | 63.70 63.40 | 6.24 6.33 | 7.43 7.48 |
| 100 | " | " | " | " | " | 7-CH₃O | diMaleate + 0.7% H₂O | $C_{30}H_{35}N_3O_9$ + 0.7% H₂O | 585.70 | 168 | Cal. Obt. | 61.52 61.29 | 6.11 5.92 | 7.18 7.14 |
| 101 | CH | CH₂ | 2-F-phenyl | 2 | $\begin{matrix}CH_3\\ \diagdown N- \\ CH_3\end{matrix}$ | H | Maleate | $C_{24}H_{26}FNO_4$ | 411.46 | 134 | Cal. Obt. | 70.05 70.15 | 6.37 6.74 | 3.40 3.47 |
| 102 | N | " | phenyl | " | " | 7-CH₃ | diHCl + 5% H₂O | $C_{20}H_{26}Cl_2N_2$ + 5% H₂O | 384.57 | 235 | Cal. Obt. | 62.46 62.15 | 7.37 7.34 | 7.29 7.21 |
| 103 | " | " | 2-CF₃-phenyl | " | " | H | diHCl + 9.5% H₂O | $C_{20}H_{23}Cl_2F_3N_2$ + 9.5% H₂O | 463.33 | 170 | NMR (CDCl₃) δppm = 6.7 to 7.8, m (8 aromatic protons); 3.75, m (H in position 3); 2.22, s $\begin{matrix}CH_3\\ (N \diagdown \\ CH_3\end{matrix}$ ); 1.8–2.95, m (2H in position 4 and CH₂—CH₂) | | |

TABLE I-continued $$\begin{array}{c} R_1 \\ | \\ N-(CH_2)_n \\ | \\ R_2 \end{array} \quad \begin{array}{c} R \\ | \\ A \\ | \\ X \end{array} \quad \begin{array}{c} R_3 \\ \end{array} \quad (I)$$

| Code Number | A | X | R | n | $\begin{array}{c} R_1 \\ | \\ N \\ | \\ R_2 \end{array}$ | R₃ | Form | Empirical Formula | Molecular Weight | Melting point (°C.) | | ELEMENTARY ANALYSIS (or NMR spectrum) | | |
|---|---|---|---|---|---|---|---|---|---|---|---|---|---|---|
| | | | | | | | | | | | % | C | H | N |
| 104 | " | " | 3-CF₃-phenyl | " | " | " | dioxalate + 1.5% H₂O | C₂₄H₂₅F₃N₂O₄ + 1.5% H₂O | 534.47 | 143 | Cal. Obt. | 53.93 53.93 | 4.89 4.59 | 5.24 5.03 |
| 105 | N | CH₂ | phenyl | 2 | $\begin{array}{c} CH_3 \\ | \\ -N \\ | \\ CH_3 \end{array}$ | 6.7-diOCH₃ | dioxolate + 4% H₂O | C₂₅H₃₀N₂O₆ + 4% H₂O | 540.28 | 170 | Cal. Obt. | 55.58 55.64 | 6.05 5.63 | 5.18 5.34 |
| 106 | " | " | " | " | $\begin{array}{c} \\ -N \bigcirc N-CH_3 \\ \end{array}$ | 5-Cl | diMaleate | C₃₀H₃₄ClN₃O₈ | 600.05 | 200 | Cal. Obt. | 60.04 59.84 | 5.71 5.77 | 7.00 6.98 |
| 107 | " | " | " | " | " | 7-OCH₃ | dioxalate + 2.3% H₂O | C₂₇H₃₃N₃O₉ + 2.3% H₂O | 556.30 | 210 | Cal. Obt. | 58.29 58.29 | 6.24 6.07 | 7.55 7.74 |
| 108 | " | " | 3-pyridyl | " | $\begin{array}{c} CH_3 \\ | \\ -N \\ | \\ CH_3 \end{array}$ | H | 1.7 oxalate + 1.4% H₂O | C₁₈H₂₁N₃ + 1.7 oxalate + 1.4% H₂O | 438.57 | 129 | Cal. Obt. | 58.60 58.27 | 5.77 5.73 | 9.58 9.50 |
| 123 | CH | CH₂ | 2-F-phenyl | 3 | $\begin{array}{c} CH_3 \\ | \\ -N \\ | \\ CH_3 \end{array}$ | H | base | C₂₁H₂₄FN | 309.41 | oil | | NMR (CDCl₃) δppm = 6.7 to 7.4, m (8 aromatic H); 5.95, nd(H in 2); 2.20, s (N(CH₃)(CH₃)) and 2.6 to 3.1, m (CH₂—N) and H in 3 and 4); 1.5, m(CH₂—CH₂—) | | |

TABLE II

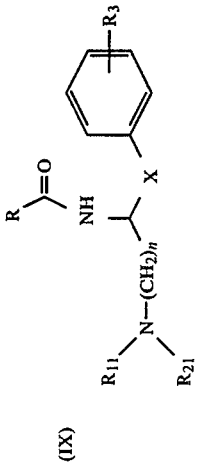

(IX)

| Code Number | R₃ | X | n | $\begin{array}{c}R_{11}\\ \diagdown N \diagup \\ R_{21}\end{array}$ | R | Form | Empirical Formula | Molecular Weight | Melting point (°C.) | ELEMENTARY ANALYSIS (or NMR spectrum) | | | |
|---|---|---|---|---|---|---|---|---|---|---|---|---|
| | | | | | | | | | % | C | H | N |
| 47 | H | $CH_2$ | 1 | $-N(CH_3)_2$ | phenyl | Base | $C_{18}H_{22}N_2O$ | 282.39 | 110 | Cal. Obt. | 76.56 76.26 | 7.85 8.02 | 9.92 10.03 |
| 48 | " | " | " | N-methylpiperazine | " | " | $C_{21}H_{27}N_3O$ | 337.45 | 156 | Cal. Obt. | 74.74 74.70 | 8.07 8.24 | 12.45 12.38 |
| 49 | " | " | " | $-N(CH_3)_2$ | 2-F-phenyl | " | $C_{18}H_{21}FN_2O$ | 300.36 | — | NMR (CDCl₃) δppm = 8 and 7.2, m, (benzenic protons); 4.40, m, (—CH—); and 2.4, m(—CH₂—CH—CH₂); 2, s, $(-N(CH_3)_2)$ | | | |
| 50 | 4-Cl | " | " | " | " | " | $C_{18}H_{20}ClFN_2O$ | 334.83 | 95 | NMR (CDCl₃) δppm = 8 and 7.21 m, (aromatic protons); 4.40, m, (—CH—); 3 and 2.4, m(CH₂—CH—CH₂); 2.22, s, $(-N(CH_3)_2)$ | | | |
| 51 | 4-F | " | " | " | phenyl | " | $C_{18}H_{21}FN_2O$ | 300.36 | 148 | Cal. Obt. | 71.47 71.85 | 7.05 7.10 | 9.33 9.29 |

TABLE II-continued (IX) Structure: R-C(=O)-NH-CH(-(CH2)n-N(R11)(R21))-X-C6H4-R3

| Code Number | R3 | X | n | R11, R21 (—N(R11)(R21)) | R | Form | Empirical Formula | Molecular Weight | Melting point (°C.) | ELEMENTARY ANALYSIS (or NMR spectrum) % | C | H | N |
|---|---|---|---|---|---|---|---|---|---|---|---|---|---|
| 52 | 4-Cl | " | " | " | " | " | C18H21ClN2O | 316.83 | 159 | Cal. | 68.23 | 6.68 | 8.84 |
|   |   |   |   |   |   |   |   |   |   | Obt. | 68.42 | 6.65 | 8.80 |
| 53 | 4-CH3 | " | " | " | " | " | C19H24N2O | 296.40 | 131 | Cal. | 76.99 | 8.16 | 9.45 |
|   |   |   |   |   |   |   |   |   |   | Obt. | 77.14 | 8.05 | 9.45 |
| 54 | 4-OCH3 | " | " | " | " | " | C19H24N2O2 | 312.40 | 137 | Cal. | 73.04 | 7.74 | 8.97 |
|   |   |   |   |   |   |   |   |   |   | Obt. | 72.94 | 7.64 | 9.03 |
| 55 | 3,4-di OCH3 | " | " | " | " | " | C20H26N2O3 | 342.42 | 140 | Cal. | 70.15 | 7.65 | 8.18 |
|   |   |   |   |   |   |   |   |   |   | Obt. | 69.98 | 7.80 | 7.96 |
| 56 | H | " | 2 | " | " | " | C19H24N2O | 296.40 | 130 | Cal. | 76.99 | 8.16 | 9.45 |
|   |   |   |   |   |   |   |   |   |   | Obt. | 77.00 | 8.35 | 9.31 |
| 57 | 2-Cl | " | " | " | " | HCl + H2O | C19H24Cl2N2O + H2O | 385.33 | 130 | Cal. | 59.21 | 6.80 | 7.27 |
|   |   |   |   |   |   |   |   |   |   | Obt. | 59.36 | 6.71 | 7.27 |
| 58 | 4-Cl | " | " | " | " | Base | C19H23ClN2O | 330.85 | 78 | NMR (CDCl3) δppm = 8.6, m, (CONH); 7.8 and 7.1m, (benzenic protons); 4.4 and 1.4 to 3, m (CH2—CH—CH2—CH2—N); 2.2, s (—N(CH3)(CH3)) | | | |
| 59 | H | " | " | " | 2-F-C6H4 | " | C19H23FN2O | 314.39 | — | NMR (CDCl3) δppm = 8, m, (CONH); 7.22, m (benzenic protons); 4.42, 2.56 and 1.68, m(—CH2—CH—CH2—CH2); 2.20, s, (—N(CH3)(CH3)) | | | |

TABLE II-continued $$\underset{R_{11}}{\overset{R_{11}}{\underset{|}{N}}} \quad \quad \underset{R_{21}}{\overset{R}{\underset{|}{\bigwedge}}} \underset{NH}{\overset{O}{\underset{|}{\bigwedge}}} \underset{R_{21}}{\overset{R_3}{\underset{|}{\bigwedge}}} \quad (IX)$$

| Code Number | R₃ | X | n | $\overset{R_{11}}{\underset{R_{21}}{N-}}$ | R | Form | Empirical Formula | Molecular Weight | Melting point (°C.) | ELEMENTARY ANALYSIS (or NMR spectrum) | | | |
|---|---|---|---|---|---|---|---|---|---|---|---|---|---|
| | | | | | | | | | | % | C | H | N |
| 60 | " | " | " | " | 3-F-C₆H₄ | " | C₁₉H₂₃FN₂O | | — | NMR (CDCl₃) δppm = 9.2, m (CONH); 7.3 m (Benzenic protons); 4.42, m (—CH—); between 1.8 and 3.4, m, (—CH₂—CH—CH₂—CH₂—N⟨CH₃/CH₃); 2.24, s, (—N⟨CH₃/CH₃) | | | |
| 61 | " | " | " | " | 4-F-C₆H₄ | " | C₁₉H₂₃FN₂O | 314.39 | 117 | Cal. Obt. | 72.58 72.72 | 7.37 7.61 | 8.91 8.68 |
| 62 | " | " | " | " | 2-Cl-C₆H₄ | " | C₁₉H₂₃ClN₂O | 330.85 | — | Cal. Obt. | 68.97 68.86 | 7.01 7.07 | 8.47 8.31 |
| 63 | " | " | " | " | 3-Cl-C₆H₄ | " | C₁₉H₂₃ClN₂O | 330.85 | — | Cal. Obt. | 68.97 68.88 | 7.01 7.19 | 8.47 8.25 |
| 64 | " | " | " | " | 4-Cl-C₆H₄ | " | " | " | 108 | Cal. Obs. | 68.97 68.92 | 7.01 7.10 | 8.47 8.21 |

TABLE II-continued $$\underset{R_{11}}{\overset{R_{21}}{\diagdown}}N-$$

$$\underset{\underset{R_{21}}{|}}{\overset{R_{11}}{|}}{N-(CH_2)_n-X-\underset{NH}{\overset{}{\underset{|}{\overset{}{C}}}}\overset{O}{\overset{\|}{\underset{}{C}}}-R}\;\;\;\;\text{with phenyl ring bearing }R_3$$

(IX)

| Code Number | R₃ | X | n | Form | R | Empirical Formula | Molecular Weight | Melting point (°C.) | ELEMENTARY ANALYSIS (or NMR spectrum) % C H N |
|---|---|---|---|---|---|---|---|---|---|
| 65 | " | " | " | " | MeO-C₆H₄- (para) | C₂₀H₂₆N₂O₂ | 326.42 | — | NMR (CDCl₃) δppm = 8.2 and 7.2, m, (benzenic protons); 7.95, m (—CONH); 4.5, m, (—CH—); 3.8, s, (CH₃O); 2,<br><br>s, (—N(CH₃)₂ ); 1.8 to 3, m<br><br>(CH₂—CH—CH₂—CH₂) |
| 66 | " | " | " | " | MeO-C₆H₄- (meta) | " | " | 70 | NMR (CDCl₃) δppm = 9, m, (CONH); 7.2, m, (benzenic protons); 3.8, s, (CH₃O); 4.40 and 1.6 to 3.4, m (—CH₂—CH—CH₂—CH₂—)<br><br>2.22, s, (—N(CH₃)₂) |
| 67 | " | " | " | " | MeO-C₆H₄- (meta) | " | 326.42 | 108 | NMR (CDCl₃) δppm = 8.2, m, (CONH); 7.0, m, (Benzenic protons); 4.2 and 1.6 to 3, m, (CH₂—CH—CH₂—CH₂—); 3.82, s,<br><br>(CH₃O); 2.08, s, (—N(CH₃)₂) |
| 68 | " | " | " | " | CH₃-C₆H₄- (ortho) | C₂₀H₂₆N₂O | 83 | NMR (CDCl₃) δppm = 7.6, m, (CONH); 7.2, m, (benzenic protons); 4.4 and from 1.6 to 3, m, (—CH₂—CH—CH₂—CH₂—); 2.30,<br><br>s, (—CH₃); 2.18, s, (—N(CH₃)₂) |

TABLE II-continued (IX) Structure: R-C(=O)-NH-CH(X-C6H4-R3)-(CH2)n-N(R11)(R21)

| Code Number | R3 | X | n | −N(R11)(R21) | R | Form | Empirical Formula | Molecular Weight | Melting point (°C.) | ELEMENTARY ANALYSIS (or NMR spectrum) |
|---|---|---|---|---|---|---|---|---|---|---|
| 69 | " | " | " | " | 3-CH3-C6H4 | " | " | " | 79 | NMR (CDCl3) δppm = 8.6, m, (CONH); 7.6 and 7.2, m, (benzenic protons); 4.4 1.6 to 3.4, m, (—CH2—CH—CH2—CH2—); 3, s, (—CH3); 2.21, s, (—N(CH3)(CH3)) |
| 70 | " | " | " | " | 3-CH3-C6H4 | " | C20H26N2O | 310.42 | — | Cal. 77.38 8.44 9.03 / Obt. 77.06 8.73 8.97 (C H N) |
| 71 | " | " | " | " | 2-NO2-C6H4 | " | C19H23N3O3 | 341.39 | — | NMR (CDCl3) δppm = 7.98, m, (CONH); 7.52, and 7.21, m, (aromatic protons); 4.30, 2.56 and 1.68, m, (—CH2—CH—CH2—CH2—); 2.20, s, (—N(CH3)(CH3)) |
| 72 | " | " | " | " | 4-NO2-C6H4 | " | " | " | — | NMR (CDCl3) δppm = 9.3, m, (CONH); 8.10 and 7.23, m (benzenic protons); 4.40, 2.80 and 1.82, m, (—CH2—CH—CH2—CH2—); 2.32, s, (—N(CH3)(CH3)) |

TABLE II-continued (IX) Structure: R-C(=O)-NH-CH with phenyl bearing R3, and N(R11)(R21)-(CH2)n- chain

| Code Number | R3 | X | n | NR11R21 | R | Form | Empirical Formula | Molecular Weight | Melting point (°C.) | ELEMENTARY ANALYSIS (or NMR spectrum) | | | |
|---|---|---|---|---|---|---|---|---|---|---|---|---|---|
| | | | | | | | | | | % | C | H | N |
| 73 | " | " | " | " | 2-Br-phenyl | — | $C_{19}H_{26}BrN_2O$ | 378.83 | — | NMR ($CDCl_3$) δppm 8.9, m, (CONH); 7.28, (benzenic protons); 4.44 and 1.6 to 3.2, m, ($-CH_2-CH-CH_2-CH_2-$); 2.18, s, ($-N(CH_3)_2$) | | | |
| 74 | " | " | " | " | cyclohexyl | " | $C_{19}H_{30}N_2O$ | 302.45 | 128 | Cal. Obt. | 75.45 75.31 | 10.00 10.15 | 9.26 9.12 |
| 75 | " | " | " | " | 2-pyridyl | " | $C_{18}H_{23}N_3O$ | 297.38 | 62 | NMR ($CDCl_3$) δppm = between 7.2 and 8.5, m, (aromatic pyridinic and amidic protons); 2.85, d, ($CH_2-\phi$); 2.20, s, ($-N(CH_3)_2$); 2.35, m, ($CH_2-N$); 1.85, m, ($CH_2-CH_2-N$) | | | |
| 76 | " | " | 3 | " | phenyl | HCl | $C_{20}H_{27}ClN_2O$ | 346.89 | 115 | Cal. Obt. | 69.24 69.23 | 7.85 7.56 | 8.08 7.90 |

TABLE II-continued (IX) structure: R-C(=O)-NH-(CH2)n-X-phenyl(R3), with N(R11)(R21) on the chain

| Code Number | R3 | X | n | R | Form | Empirical Formula | Molecular Weight | Melting point (°C.) | | % | C | H | N |
|---|---|---|---|---|---|---|---|---|---|---|---|---|---|
| 77 | " | " | " | 2-fluorocyclohexyl | Base | $C_{20}H_{25}FN_2O$ | 328.42 | 73 | Cal.<br>Obt. | | 73.14<br>73.27 | 7.67<br>7.81 | 8.53<br>8.41 |
| 78 | " | $CH_2-O$ | 1 | phenyl | HCl | $C_{18}H_{23}ClN_2O_2$ | 334.84 | 182 | Cal.<br>Obt. | | 64.56<br>64.63 | 6.92<br>7.01 | 8.37<br>8.33 |
| 79 | " | " | " | 2-fluorophenyl | Base | $C_{18}H_{21}FN_2O_2$ | 316.36 | Oil | Cal.<br>Obt. | | 68.92<br>68.16 | 6.69<br>6.70 | 8.88<br>8.95 |
| 80 | " | " | " | 3-fluorophenyl | " | " | " | " | NMR (CDCl$_3$) $\delta$ppm = 7.22, m, (aromatic protons and CONH); 4.40, m, (O—CH$_2$—CH—); 2.24, s, (N(CH$_3$)(CH$_3$)); 2.60, m, (—CH$_2$—N(  )) | | | | |
| 81 | " | " | " | 4-fluorophenyl | " | " | " | " | Cal.<br>Obt. | | 68.33<br>68.36 | 6.69<br>6.97 | 8.86<br>8.66 |

TABLE II-continued

Structure (IX):

R-C(=O)-NH-(CH₂)ₙ-X-C₆H₄(R₃), with amine N(R₁₁)(R₂₁)

| Code Number | R₃ | X | n | NR₁₁R₂₁ | R | Form | Empirical Formula | Molecular Weight | Melting point (°C.) | | ELEMENTARY ANALYSIS (or NMR spectrum) % | | |
|---|---|---|---|---|---|---|---|---|---|---|---|---|---|
| | | | | | | | | | | | C | H | N |
| 82 | " | " | " | " | 2-chloro-cyclohexyl | " | C₁₈H₂₁ClN₂O₂ | 332.82 | <50 | Cal. Obt. | 64.95 65.45 | 6.36 6.58 | 8.42 8.23 |
| 83 | " | " | " | " | 3-chlorophenyl | Base + 4/5 H₂O | C₁₈H₂₁ClN₂O₂ + 4/5 H₂O | 347.23 | oil | Cal. Obt. | 62.26 62.35 | 6.36 6.28 | 8.07 7.79 |
| 84 | " | " | " | " | 4-chloro-cyclohexyl | Base | C₁₈H₂₁ClN₂O₂ | 332.82 | " | Cal. Obt. | 64.95 63.03 | 6.36 6.48 | 8.42 7.97 |
| 85 | " | " | 2 | " | phenyl | " | C₁₉H₂₄N₂O₂ | 312.39 | — | NMR (CDCl₃) δppm 8.8, m, (CONH); 7.8 and 7.3, m (benzenic protons); 4.45 and 1.75 to 3.10, m, (—CH—CH₂—CH₂—N(CH₃)₂); 4.20, m, (O—CH₂); 2.2, s, (—N(CH₃)₂) | | | |

TABLE II-continued $$\underset{(IX)}{\overset{R-\overset{O}{\underset{NH}{\overset{\|}{C}}}-\overset{}{\underset{\underset{R_{21}}{|}}{\overset{|}{C}H}}-(CH_2)_n-X-\underset{R_3}{\overset{}{\bigcirc}}}{}}$$

| Code Number | R$_3$ | X | n | $\begin{array}{c}R_{11}\\ \diagdown\\ N\\ \diagup\\ R_{21}\end{array}$ | R | Form | Empirical Formula | Molecular Weight | Melting point (°C.) | ELEMENTARY ANALYSIS (or NMR spectrum) |
|---|---|---|---|---|---|---|---|---|---|---|
| 109 | 2-Cl | CH$_2$ | 1 | piperazine with N—CH$_3$ | phenyl | | C$_{21}$H$_{26}$ClN$_3$O | 371.89 | 180 | NMR (CDCl$_3$ + DMSO) δppm 6.6 to 7.8, m (9 aromatic H and CONH); 4.40, m (CH—); 3.2, m (—CH$_2$—); 2.2 to 2.65, m (CH$_2$—N(CH$_2$—CH$_2$)$_2$N—); 2.2, s, (N—CH$_3$) |
| 110 | 4-CH$_3$ | " | " | Et$_2$N— | " | " | C$_{21}$H$_{28}$N$_2$O | 324.45 | 117 | NMR (CDCl$_3$) δppm = 7 to 7.8, m (9 aromatic H); 6.5, m (CONH); 4.2, m (CH—); 3, m (—CH$_2$—); 2.5, q (N(CH$_2$)$_2$); 2.6, d (CH$_2$—N); 2.45, s (—CH$_3$); 1.92, t (2CH$_3$) |
| 111 | " | " | " | pyrrolidine | " | " | C$_{21}$H$_{26}$N$_2$O | 322.43 | 134 | NMR (CDCl$_3$) δppm = 7 to 7.8, m (9 aromatic H); 6.4, m (CONH); 4.3, m (CH—); 3, m (—CH$_2$—); 2.5, m (CH$_2$—N(CH$_2$CH$_2$)$_2$); 2.3, s (CH$_3$); 1.5, m (N(CH$_2$CH$_2$)$_2$) |

TABLE II-continued (IX) Structure: R-C(=O)-NH-CH(-(CH₂)ₙ-N(R₁₁)(R₂₁))-C₆H₄-X-R₃

| Code Number | R₃ | X | n | $\begin{matrix}R_{11}\\ \diagdown\\ N\\ \diagup\\ R_{21}\end{matrix}$ | R | Form | Empirical Formula | Molecular Weight | Melting point (°C.) | ELEMENTARY ANALYSIS (or NMR spectrum) C % / H / N |
|---|---|---|---|---|---|---|---|---|---|---|
| 112 | " | " | " | piperidine (N-containing 6-ring) | " | " | C₂₂H₂₈N₂O | 336.46 | 162 | NMR (CDCl₃) δppm = 7 to 7.8, m (9 aromatic H); 6.5, m (CONH); 4.38, m (CH—); 3, m(CH₂)₂ (CH₂); 2.28, s (CH₃); 2.38, m (CH₂—N<CH₂-CH₂>CH₂-CH₂); 1.5, m (N-CH₂-CH₂-CH₂). |
| 113 | " | " | " | morpholine | " | " | C₂₁H₂₆N₂O₂ | 338.43 | 195 | NMR (CDCl₃) δppm = 7 to 7.8, m (9 aromatic H); 6.6, m (CONH); 4.42, m (CH); 3.64, t (—N<CH₂-CH₂>O); 3, d (—CH₂—); 2.44, m (CH₂—N<CH₂-CH₂>O-CH₂-CH₂); 2.3, s (CH₃). |
| 114 | 4-CH₃ | " | " | N-methylpiperazine | " | " | C₂₂H₂₉N₃O | 351.48 | 147 | NMR (CDCl₃ δppm = 7 to 7.8, m (9 aromatic H); 6.45, m (CONH); 4.4, m (CH—); 3, s (CH₂); 3.42, m (—CH₂—N<...>N); 2.38, s (CH₃); 2.20, s (N—CH₃) |

TABLE II-continued

Structure (IX):
R-C(=O)-NH-CH(aryl with R₃)-(CH₂)ₙ-N(R₁₁)(R₂₁)

| Code Number | R₃ | X (−N(R₁₁)(R₂₁)) | n | R | Form | Empirical Formula | Molecular Weight | Melting point (°C.) | ELEMENTARY ANALYSIS (or NMR spectrum) |
|---|---|---|---|---|---|---|---|---|---|
| 115 | 4-CH₃O | " | " | " | " | C₂₂H₂₉N₃O₂ | 367.48 | 132 | NMR (CDCl₃) δppm = 6.7 to 7.8, m (9 aromatic H); 6.5, m (CONH); 4.4, m (—CH—); 3.75, s (CH₃O); 3, d (CH₂); 2.4, m (CH₂—N piperazine); 2.20, s (N—CH₃) |
| 116 | H | −N(CH₃)(CH₃) | 2 | 2-CF₃-phenyl | " | C₂₀H₂₃F₃N₂O | 364.40 | 76 | NMR (CDCl₃) δppm = 7 to 7.8, m (9 aromatic N and CONH); 4.30, m (—CH); 3, d (CH₃); 2.4, m (CHG₂—N(CH₃)(CH₃)); 2.4, s |
| 117 | " | " | " | 3-CF₃-phenyl | " | C₂₀H₂₃F₃N₂O | 364.40 | 100 | NMR (CDCl₃) δppm = 9.65, m (CONH); 7.2 to 8, m (9 aromatic H); 4.4, m (—CH); 2.25, s (—N(CH₃)(CH₃)); 2.2 to 3.2, m (CH₂—CH₂—NH); 1.6, m (CH₂) |

TABLE II-continued (IX) Structure: R-C(=O)-NH-CH(-(CH2)n-N(R11)(R21)) with R3-substituted phenyl-X group

| Code Number | R3 | Form | X | n | $\overset{R_{11}}{\underset{R_{21}}{\diagdown}}N-$ | R | Empirical Formula | Molecular Weight | Melting point (°C.) | ELEMENTARY ANALYSIS (or NMR spectrum) C % H N |
|---|---|---|---|---|---|---|---|---|---|---|
| 119 | H | " | " | " | " | 3-pyridyl | C18H23N3O | 297.39 | 100 | NMR (CDCl3) δppm = 9.3, m (CONH); 9.25, 8.95 and 8.20, m (3 pyridinic H); 7.3, m (5 aromatic H and 1 pyridinic H); 4.4, m (CH); 2.3, s (N(CH3)2); 2.3 to 3.4, m (CH2—N); 1.75, m (CH2) |
| 120 | 3,4-di CH3O | " | " | " | " | phenyl | C21H28N2O3 | 356.45 | 115 | NMR (CDCl3) δppm = 9, m (CONH); 7.8, 7.4, m and 6.8, s (8 aromatic H); 4.4, m (CH); 3.8, s (2CH3O); 2.22, s (—N(CH3)2); 2.3 to 3.2, m (CH2—N); 1.65, m (CH2) |
| 118 | 2-Cl | " | " | " | N-methylpiperazinyl | phenyl | C22H28N3ClO | 385.92 | 180 | NMR (CDCl3) δppm = 8.2 8.5, m (aromatic H in α of Cl); 7 to 8, m (8 aromatic H and CONH); 4.45, m (CH); 3.15, m (CH2); 2.2 2.8, m (10 H : CH2—N, N—); 2.2, s (CH3—); 1.8, m (CH2) |

TABLE III $$\underset{R_{21}}{\overset{R_{11}}{N}}-(CH_2)_n-\underset{X}{\overset{NH_2}{CH}}-C_6H_4-R_3 \quad (XV)$$

| Code Number | $R_3$ | X | n | $-N\begin{smallmatrix}R_{11}\\R_{21}\end{smallmatrix}$ | Form | Empirical Formula | Molecular Weight | Melting Point (°C.) | ELEMENTARY ANALYSIS (or NMR spectrum) |
|---|---|---|---|---|---|---|---|---|---|
| 89 | H | $CH_2$ | 2 | $-N(CH_3)_2$ | Base | $C_{12}H_{20}N_2$ | 192.29 | oil | NMR (CDCl$_3$), δppm = 7.21, m, (benzenic protons); between 2.3 and 3.2, m(CH$_2$—CH(CH$_3$)—CH$_2$—CH$_2$); 2.2, s (—N(CH$_3$)$_2$); 1.5, m (CH$_2$—CH$_2$—N⟨) |
| 90 | 2Cl | " | " | " | " | $C_{12}H_{19}ClN_2$ | 226.74 | " | NMR (CDCl$_3$), δppm = 7.2, m, (benzenic protons); 2.2, s, (—N(CH$_3$)$_2$); 1.9, s, (—NH$_2$); 1.4 to 3, m, (CH$_2$—CH—CH$_2$—CH$_2$—) |
| 91 | 4-Cl | " | " | " | " | $C_{12}H_{19}ClN_2$ | 226.74 | " | NMR (CDCl$_3$), δppm = 7.2, m, (benzenic protons); 1.3 to 3.2, m, (CH$_2$—CH—CH$_2$—CH$_2$—); 2.3, s (—N(CH$_3$)$_2$); 1.8, m (—NH$_2$) |
| 92 | H | " | 3 | " | " | $C_{13}H_{22}N_2$ | 206 | " | NMR (CDCl$_3$), δppm = 7.2, m, (benzenic protons); between 1.2 and 3.6, m (CH$_2$—CH(CH$_3$)—CH$_2$—CH$_2$—CH$_2$—); 2.18, s, (—N(CH$_3$)$_2$) |
| 93 | H | $CH_2O$ | 1 | $-N(CH_3)_2$ | Dioxalate | $C_{15}H_{22}N_2O_9$ | 374,34 | 163 | %    C    H    N<br>Cal. 48.12   5.92   7.48<br>Obt. 48.08   5.80   7.53 |
| 121 | 3,4-diCH$_3$O | $CH_2$ | 2 | $-N(CH_3)_2$ | Base | $C_{14}H_{24}N_2O_2$ | 252,35 | oil | NNMR (CDCl$_3$) δppm = 6.8, s (3 aromatic H); 3.90, s (2CH$_3$O); 2.2, s (—N(CH$_3$)$_2$) 2.3 to 3.2, m (CH$_2$—CH(H)—CH$_2$—N); 1.6, m (NH$_2$ CH$_2$—N⟨) |

TABLE III-continued

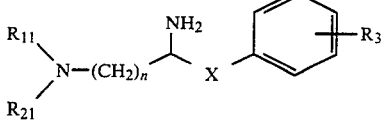

| Code Number | R₃ | X | n | $\begin{array}{c}\phantom{x}\phantom{x}R_{11}\\-N\\\phantom{x}\phantom{x}R_{21}\end{array}$ | Form | Empirical Formula | Molecular Weight | Melting Point (°C.) | ELEMENTARY ANALYSIS (or NMR spectrum) |
|---|---|---|---|---|---|---|---|---|---|
| 122 | 2-Cl | " | 2 | 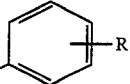 | Base | C₁₅H₂₄ClN₃ | 281,82 | oil | NMR (CDCl₃) δppm = 7.2, m (4 aromatic H); 2.45, s 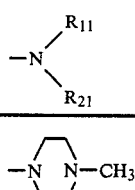 ( N—CH₃); 2.2 to 3.2, m (13 H; 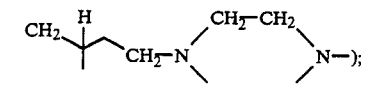 ); 1.6, m (CH₂ N and NH₂). |

The compounds of formula (I) were studied on laboratory amimals and showed activities in the field of the central nervous system as analgesics and antidepressants.

The analgesic activity was demonstrated in mice by i.p. administration of the compounds of formula (I) using the phenylbenzoquinone test according to the method described by E. Siegmund in Proced. Soc. Exp. Biol. and Med. 95, 729, (1957).

The antidepressive activity was demonstrated in mice by the antagonism to ptosis observed an hour after an intravenous injection of reserpine (2 mg/kg) in mice according to the method described by C. Gouret and J. Thomas in J. Pharmacol. (Paris) (1973), 4, 401.

To illustrate the invention, there are shown in table IV below, the results obtained in these two tests and the acute toxicity (LD 50) of some compounds of formula (I).

TABLE IV

| Code Number | LD 50 toxicity (mg/kg/i.p.) | ED 50 analgesic property (mg/kg/i.p.) | ED 50 antidepressive property (mg/kg/i.p.) |
|---|---|---|---|
| 1 | 62 | 6 | 10 |
| 2 | 110 | 7.3 | 1 |
| 6 | 41 | 5 | 3.5 |
| 7 | 170 | 6.2 | 10 |
| 8 | 35 | 2.3 | 1.1 |
| 9 | 52 | 3 | 4.3 |
| 10 | 60 | 4 | 2.8 |
| 11 | 37 | 3 | 0.8 |
| 12 | 50 | 5 | 15 |
| 13 | 65 | 3 | — |
| 14 | 135 | 15 | — |
| 15 | 67 | 10 | 0.9 |
| 16 | 65 | 10 | 8.2 |
| 17 | 65 | 6 | 1.5 |
| 18 | 70 | 1 | — |
| 19 | 95 | 4 | 3.8 |
| 20 | 62 | 3.7 | 1.8 |
| 21 | 70 | 10 | 1.2 |
| 22 | 70 | 6.2 | 0.6 |
| 23 | 55 | 2 | 2 |
| 24 | 61 | 8.4 | 2.1 |
| 25 | 60 | 3.8 | 3.7 |
| 26 | 65 | 7.6 | 5.4 |
| 27 | 70 | 11 | 4.4 |
| 28 | 42 | 10 | 3 |
| 29 | 78 | 10 | 6.8 |
| 30 | 70 | — | 4.2 |
| 31 | 50 | 5.6 | 1.8 |
| 32 | 67 | 6.6 | 6.6 |
| 33 | 70 | 8.8 | 2.7 |
| 34 | 77 | 3.4 | 1 |
| 35 | 80 | 8 | 8 |
| 36 | 77 | — | 2.4 |
| 37 | 82 | 10 | 10 |
| 38 | 85 | — | 3.4 |
| 39 | 100 | 1.9 | 0.7 |
| 40 | 80 | 3 | — |
| 41 | 62 | 7.2 | 3.5 |
| 42 | 70 | 3.5 | 7 |
| 43 | 65 | 10 | 3 |
| 44 | 130 | 9.8 | 10 |
| 45 | 160 | 16.5 | 12 |
| 86 | 94 | 10 | 4 |
| 87 | 100 | — | 30 |
| 94 | 140 | 22 | — |
| 95 | 45 | 10 | — |
| 97 | 52 | 10 | — |
| 98 | 125 | 30 | — |
| 99 | 130 | 30 | — |
| 100 | 140 | 30 | 9 |
| 101 | 93 | 4.3 | 0.4 |
| 103 | 70 | — | 3.8 |
| 104 | 62 | 4.3 | — |
| 105 | 165 | 12 | 30 |
| 106 | 145 | 12 | — |
| 108 | 90 | 7.6 | 12 |

The difference between the toxic doses and the actives doses allows the compounds of formula (I) to be used in therapeutic, especially as analgesics and antidepressants. The present invention concerns also pharmaceutical compositions comprising at least one compound of formula (I) in association with a pharmaceutically acceptable carrier. These compositions will be preferably aministrated:

orally in the form of tablets, pills, etc . . . in quantities up to 200 mg in 3 or 4 doses per day, intravenously, in the form of injectable phials in quantities up to 60 mg in 3 or 4 doses per day, intramuscularly in the form of injectable phials, in quantities up to 90 mg in 3 or 4 doses per day, or in the form of suppositories in quantities up to 200 mg in 3 or 4 doses per day.

We claim:

1. A compound having the formula

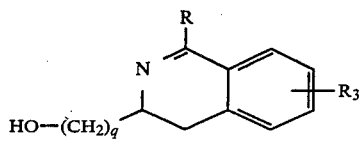

wherein q is 2 or 3; R is phenyl, halophenyl, nitrophenyl, alkylphenyl in which the alkyl group has 1 to 4 carbon atoms, alkoxyphenyl in which the alkoxy group has 1 to 4 carbon atoms, trifluoromethylphenyl, pyridyl or cyclohexyl; and $R_3$ is halogen, hydrogen, alkyl having 1 to 4 carbon atoms, alkoxy having 1 to 4 carbon atoms or two methoxy groups.

2. A compound as claimed in claim 1 in which q is 2, $R_3$ is hydrogen and R is ortho-fluorophenyl.

* * * * *